(12) United States Patent
Li

(10) Patent No.: US 10,842,441 B2
(45) Date of Patent: Nov. 24, 2020

(54) ADAPTIVE METHODS AND SYSTEMS FOR DETECTING SIGNALS FROM INTERFERENCE CONTAMINATED DATA

(71) Applicant: Xinde Li, Etobicoke (CA)

(72) Inventor: Xinde Li, Etobicoke (CA)

(*) Notice: Subject to any disclaimer, the term of this patent is extended or adjusted under 35 U.S.C. 154(b) by 298 days.

(21) Appl. No.: 15/555,847

(22) PCT Filed: Mar. 14, 2016

(86) PCT No.: PCT/CA2016/050281
§ 371 (c)(1),
(2) Date: Sep. 5, 2017

(87) PCT Pub. No.: WO2016/145522
PCT Pub. Date: Sep. 22, 2016

(65) Prior Publication Data
US 2018/0035951 A1 Feb. 8, 2018

Related U.S. Application Data

(60) Provisional application No. 62/132,903, filed on Mar. 13, 2015.

(51) Int. Cl.
*A61B 5/00* (2006.01)
*A61B 5/022* (2006.01)
*A61B 5/12* (2006.01)

(52) U.S. Cl.
CPC ........ *A61B 5/7203* (2013.01); *A61B 5/02225* (2013.01); *A61B 5/12* (2013.01);
(Continued)

(58) Field of Classification Search
CPC ..... A61B 5/02225; A61B 5/12; A61B 5/7203; A61B 5/721; A61B 5/725; A61B 5/742
See application file for complete search history.

(56) References Cited

U.S. PATENT DOCUMENTS 6,463,411 B1  10/2002  Li et al.
6,620,104 B2   9/2003  Tamura et al.
(Continued)

FOREIGN PATENT DOCUMENTS

CN   101785670 A    7/2010
CN   102008297 A    4/2011
(Continued)

OTHER PUBLICATIONS

International Search Report and Written Opinion dated Jun. 14, 2016 in corresponding International Patent Application No. PCT/CA2016/050281.
(Continued)

*Primary Examiner* — Christine H Matthews
(74) *Attorney, Agent, or Firm* — Bereskin & Parr LLP/S.E.N.C.R.L., s.r.l.; Tony Orsi

(57) ABSTRACT

Various embodiments are described herein for a system and method for adaptively detecting a desired signal S(n) in a noisy environment. A main signal is obtained that the desired signal and at least one of noise and interference from a collective noise source, an auxiliary signal is obtained comprising a version of the noise and/or a version of the interference from the collective noise source; and at a processing unit at least one signal feature is defined, noise and interference components corresponding to the noise and/or interference and the version of the noise and/or version of the interference are defined, and strengths thereof are estimated. The desired signal is estimated using the at least one signal feature and corresponding strengths, and the noise and/or interference components are estimated using the components and corresponding strengths.

42 Claims, 19 Drawing Sheets

(52) U.S. Cl.
CPC .............. *A61B 5/721* (2013.01); *A61B 5/725* (2013.01); *A61B 5/742* (2013.01)

(56) References Cited

U.S. PATENT DOCUMENTS

| | | |
|---|---|---|
| 7,536,262 B2 | 5/2009 | Hornbostel et al. |
| 2014/0018635 A1 | 1/2014 | Buchheim et al. |

FOREIGN PATENT DOCUMENTS

| | | |
|---|---|---|
| CN | 104382614 A | 3/2015 |
| DE | 2531242 A1 | 1/1976 |
| EP | 2152895 A2 | 2/2010 |
| JP | 2007-125246 A | 5/2007 |
| JP | 2013-239548 A | 11/2013 |

OTHER PUBLICATIONS

James, et al., "Contralateral suppression of DPOAE measured in real time", Clin Otolaryngol., 2002; 27(2): 106-112.

Konomi, et al., "Age related changes to the dynamics of contralateral DPOAE suppression human subjects", J Otolaryngol Head Neck Surg., 2014; 43(1): 15 (9 pages).

Wolter, et al., "Separating the contributions of olivocochlear and middle ear muscle reflexes in modulation of distortion product otoacoustic emission levels", Audiol Neurootol., 2014; 19(1): 41-48.

Stengel, "Optimal control and estimation", Courier Corporation, 2012, pp. 400-402.

Babbs, "Oscillometric measurement of systolic and diastolic blood pressures validated in a physiologic mathematical model", BioMedical Engineering OnLine, 2012; 11: 56 (22 pages).

James, et al., "Dynamics of real time DPOAE contralateral suppression in chinchillas and humans", International Journal of Audiology, 2005, 44(2): 118-129.

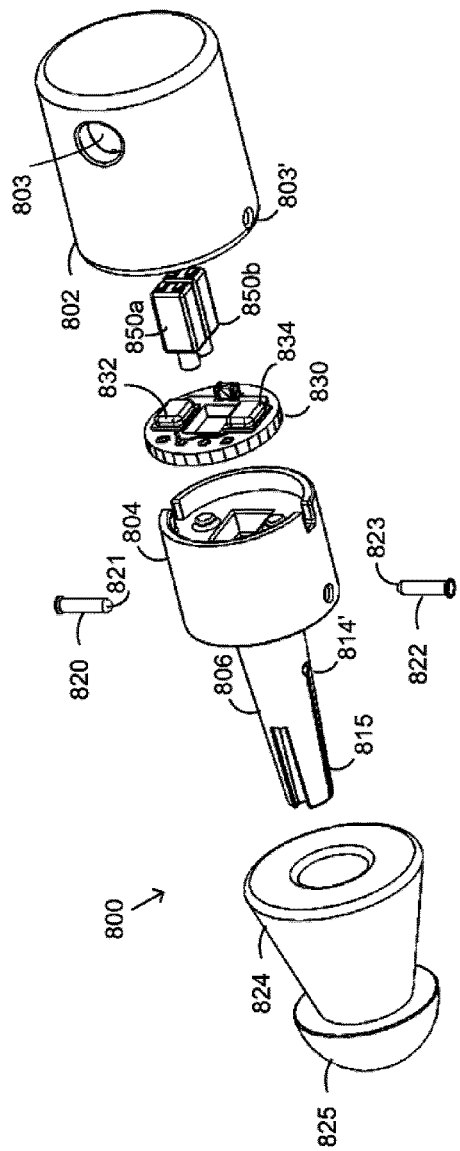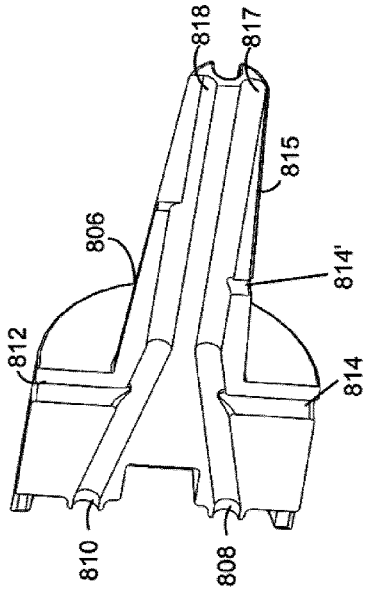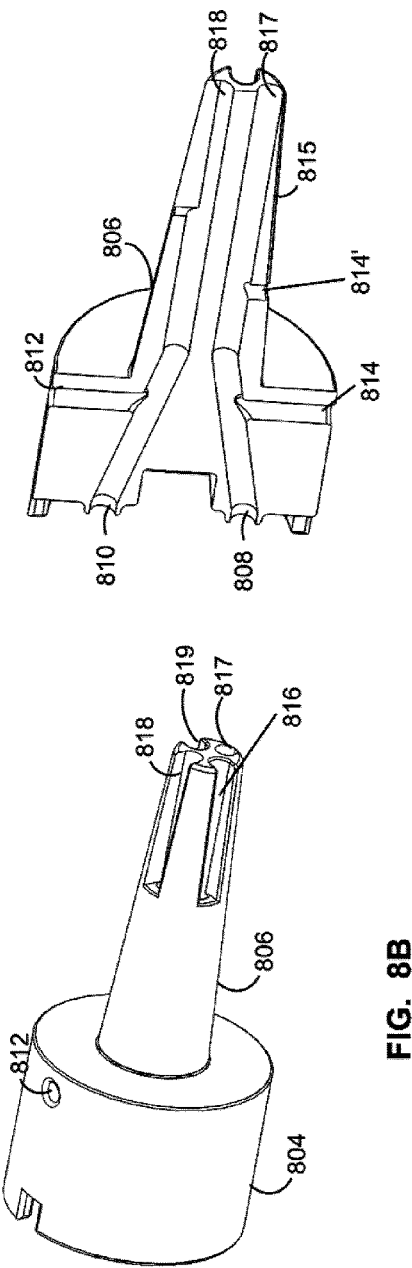
FIG. 8A
FIG. 8C
FIG. 8B

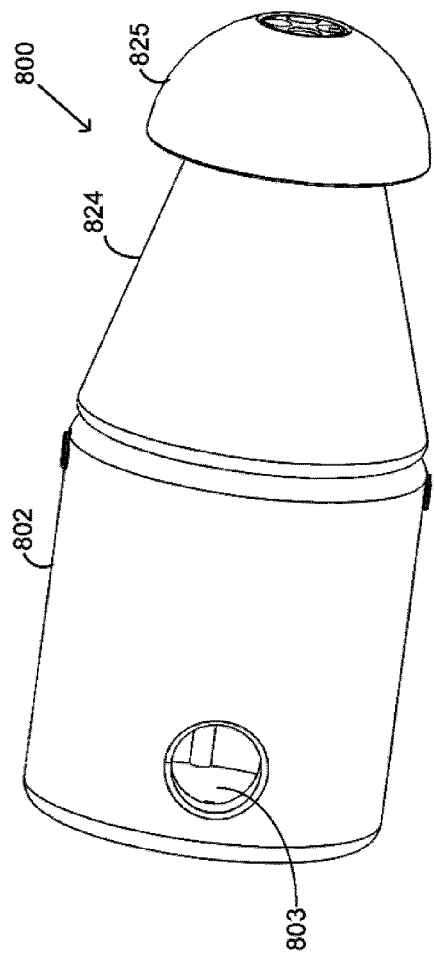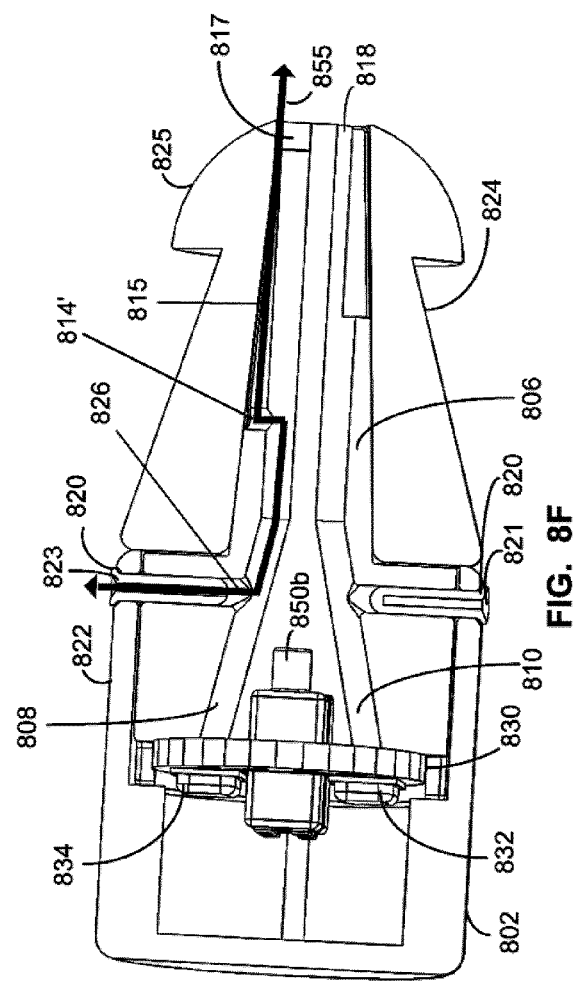
FIG. 8E
FIG. 8F

ADAPTIVE METHODS AND SYSTEMS FOR DETECTING SIGNALS FROM INTERFERENCE CONTAMINATED DATA

CROSS-REFERENCE TO RELATED APPLICATION

This application claims the benefit of U.S. Provisional Patent Application No. 62/132,903 filed Mar. 13, 2015; the entire contents of Patent Application No. 62/132,903 are hereby incorporated by reference.

FIELD

Various embodiments are described herein for an apparatus and method that may be used to detect weak signals or signals contaminated with noise and/or interference in a variety of different applications.

BACKGROUND

The ability to reliably detect a weak signal or a signal distorted by noise and/or signal artifacts is needed in many applications. Generally, the quality of a signal relative to the noise and other forms of distortion that may be present is expressed by the signal-to-noise ratio (SNR). A low SNR may indicate that a signal of interest may be highly distorted and detection of this signal may be difficult using conventional techniques.

For example, in medical applications, many physiologically relevant signals may be weak compared with background noise and signal artifacts captured during the recording of these signals. In other words, the SNR of these physiologically relevant signals is low. As a result of distortions such as noise and signal artifacts the difficulty and challenges associated with reliability detecting inherently weak signals are therefore high. Accordingly, there is a need for systems and methods which are capable of facilitating detection of inherently weak or highly distorted signals efficiently. Within medical applications there is also a desire to do so with the least degree of invasiveness and discomfort for a patient.

SUMMARY OF VARIOUS EMBODIMENTS

In a broad aspect, at least one embodiment described herein provides a method for adaptively detecting a desired signal $S(n)$ in a noisy environment, the method comprising: obtaining a main signal $Z(n)$ comprising the desired signal $S(n)$ and at least one of noise and interference $V(n)$ from a collective noise source; obtaining an auxiliary signal $Y(n)$ comprising at least one of a version of the noise and a version of the interference from the collective noise source; and at a processing unit: generating a feature data set having at least one signal feature element for defining at least one feature of the desired signal; generating noise and interference components corresponding to the at least one of noise and interference $V(n)$ and the at least one version of the noise and the version of the interference $Y(n)$; estimating strengths of the at least one signal feature, the at least one noise and interference $V(n)$ components and the at least one version of the noise and the version of the interference $Y(n)$ components; and estimating the desired signal $S(n)$ using the at least one signal feature and corresponding strengths, the at least one of noise and interference $V(n)$ components and corresponding strengths and the at least one version of the noise and the version of the interference $Y(n)$ components and corresponding strengths.

In at least some embodiments, the method may further comprise using quasi-Kalman filtering for estimating strengths and the desired signal by: defining an observation matrix $H(n)$ to include the at least one signal feature elements, data values for the at least one noise and interference $V(n)$ components and data values for the at least one version of the noise and the version of the interference $Y(n)$ components; defining a state vector $X(n)$ comprising strengths for the at least signal feature, model parameters for the at least one noise and interference $V(n)$ components and model parameters for the at least one version of the noise and the version of the interference $Y(n)$ components; defining a state equation for $X(n)$ based on a combination of $X(n)$ for a previous time stamp $X(n-1)$ and noise at a previous time stamp $u(n-1)$; and using a quasi-Kalman filtering method to estimate the state equation and the model parameters.

In at least some embodiments, the method may further comprise: defining a time varying signal feature matrix $F(n)$, the linear combination of elements in the signal feature matrix defining the desired signal $S(n)$ of the main signal $Z(n)$; defining a time varying noise and interference matrix, the linear combination of elements in the noise and interference matrix defining the at one noise and interference portion $V(n)$ of the main signal $Z(n)$; and defining an observation matrix $H(n)$ comprising $F(n)$, $Y(n)$ and $V(n)$, and an observation equation to describe the main signal $Z(n)$ as a linear combination of elements of the state vector.

In at least some embodiments, the method may further comprise constructing signal component waveforms by a linear combination of the estimated state vector and said feature matrix.

In at least some embodiments, the method may further comprise constructing interference component waveforms by a linear combination of the estimated state vector and the noise and interference matrix.

In at least some embodiments, the method may further comprise updating noise and interference matrix components using real time data from the auxiliary signal and using the estimated state vector so the method performs adaptive filtering.

In at least some embodiments, the method may comprise generating the at least one signal feature from a closed-form formula, a look-up table or an actual recording having specific characteristics based on the desired signal that is to be detected.

In at least some embodiments, the method may comprise relating the at least one of noise and interference components $V(n)$ components and the at least one of a version of the noise and a version of the interference $Y(n)$ components by a linear system.

In at least some embodiments, the method may comprise defining the linear system using a time-varying Autoregressive Moving Average (ARMA) model.

In at least some embodiments, the method may comprise generating the at least one of noise and interference components $V(n)$ components and the at least one of a version of the noise and a version of the interference $Y(n)$ components by using at least one of characteristics from noise and interference time functions, data from the auxiliary signal, and/or estimates provided by the processing unit thereby making the modeling adaptive to real data.

In at least some embodiments, the method comprises using a main sensor to obtain the main signal $Z(n)$ and using an auxiliary sensor to obtain the auxiliary signal $Y(n)$.

In at least some embodiments, the method may be applied to Distortion Product Otoacoustic Emission (DPOAE) measurements, and the method may further comprise using a probe having two speakers to provide two stimulus tones to a subject, a main microphone to record the main signal $Z(n)$ and an auxiliary microphone to record the auxiliary signal $Y(n)$.

In at least some embodiments, the at least one signal feature comprises signal features corresponding to a first stimulus tone, a second stimulus tone, and a DPOAE signal and the noise and interference $V(n)$ and $Y(n)$ components are obtained from the auxiliary signal.

In at least some embodiments, the method may be applied to DPOAE suppression measurements and the at least one signal feature further comprises signal features corresponding to a tone with a frequency adjacent to the DPOAE tone for noise floor estimation.

In at least some embodiments, the method may be applied to monitor the occurrence of middle ear muscle reflex (MEMR), by detecting a phase change of a primary tone or an intentionally introduced tone between a time period when a suppressor is on and when the suppressor is off, and determining the MEMR occurrence by comparing the phase change to a threshold.

In at least some embodiments, the method may be applied to oscillometric blood pressure monitoring, the method further comprising using a blood pressure cuff with conduits for sensing a main pressure and an auxiliary pressure, a main pressure sensor to obtain the main signal $Z(n)$, and a combination sensor having an auxiliary pressure sensor.

In at least some embodiments for blood pressure monitoring, the combination sensor may further comprise an accelerometer to obtain the auxiliary signal $V(n)$, the accelerometer being used for sensing physical artifacts during monitoring.

In at least some embodiments for blood pressure monitoring, the at least one signal feature may be a single constant element and the noise and interference components $V(n)$ and $Y(n)$ are based on data collected from the auxiliary signal.

In at least some embodiments for blood pressure monitoring, the estimated desired signal may be used to estimate systolic and diastolic pressures using standard methods comprising determining oscillation envelope slope change during cuff deflation or determining a maxima of the envelope.

In at least some embodiments, the method may further be applied to continuous blood pressure monitoring with integrated calibration, wherein the at least one signal feature comprises elements 1 $(P_s-P_C)$ $(P_C-P_{C0})$ $(P_s-P_C)(P_c-P_{C0})$ $(P_C-P_{C0})^2$ wherein $P_c(n)$ corresponds to a moving average of the pressure imparted by the blood pressure cuff, and $P_{sv}(n)$ corresponds to a pressure peak or minimum of the blood pressure cuff at the moving average value $P_c(n)$; the state vector is defined as $X(n)=X(n)=[d_0(n)\ d_1(n)\ \ldots\ d_5]^T$; and the main signal $Z(n)=P_{sys}-P_C(n)$ or $Z(n)=P_{dia}-P_c(n)$ where $P_{sys}$ is the estimated systolic pressure and $P_{dia}$ is the estimated diastolic pressure.

In at least some embodiments for continuous blood pressure monitoring with integrated calibration, components may not be needed for the noise and interference $V(n)$ or $Y(n)$ and the observation matrix $H(n)$ is defined by the signal features matrix $F(n)$.

In at least some embodiments for continuous blood pressure monitoring with integrated calibration, the method may comprise determining a real time continuous blood pressure waveform according to:

$$P_b = P_c + g(P_s - P_c, P_c) = P_c + d_0 + d_1(P_s - P_C) + d_2(P_C - P_{C0}) + d_3(P_s - P_C)^2 + d_4(P_s - P_C)(P_c - P_{C0}) + d_5(P_C - P_{C0})^2$$

In at least some embodiments for continuous blood pressure monitoring with integrated calibration, the strengths for the at least one signal feature may be obtained by performing calibration comprising determining a blood pressure measurement to obtain a systolic and a diastolic pressure; setting the pressure applied by the blood pressure cuff to a value that is about J mmHg above the diastolic pressure; decreasing the pressure applied by the blood pressure cuff at a rate that is less than 0.5 mmHg per second and recording a plurality of data pairs wherein each pair comprises a pulse pressure and a corresponding cuff pressure until the pressure applied by the pressure cuff is about K mmHg below the diastolic pressure; identifying, from the plurality of data pairs, at least one data pair in which the pulse pressure corresponds to a detected pulse pressure peak or a detected pulse pressure valley; and determining at least one calibration parameter based on the measured systolic pressure, diastolic pressure and the at least one identified data pair.

In another broad aspect, at least one embodiment described herein provides a computer readable medium comprising a plurality of instructions executable on a processing unit for adapting the processing unit to implement a method of adaptively detecting a desired signal in a noisy environment, the computer readable medium comprising instructions for performing at least one embodiment of the methods described in accordance with the teachings herein.

In another broad aspect, at least one embodiment described herein provides a system for adaptively detecting a desired signal $S(n)$ in a noisy environment, the system comprising: inputs for obtaining a main signal $Z(n)$ and an auxiliary signal $Y(n)$, the main signal comprising $Z(n)$ comprising the desired signal $S(n)$ and at least one of noise and interference $V(n)$ from a collective noise source, and the auxiliary signal $Y(n)$ comprising at least one of a version of the noise and a version of the interference from the collective noise source; and a processing unit that is coupled to the inputs, the processing unit being configured to: generate a feature data set having at least one signal feature element for defining at least one feature of the desired signal; generating noise and interference components corresponding to the at least one of noise and interference $V(n)$ and the at least one version of the noise and the version of the interference $Y(n)$; estimate strengths of the at least one signal feature, the at least one noise and interference $V(n)$ components and the at least one version of the noise and the version of the interference $Y(n)$ components; and estimate the desired signal $S(n)$ using the at least one signal feature and corresponding strengths, the at least one of noise and interference $V(n)$ components and corresponding strengths and the at least one version of the noise and the version of the interference $Y(n)$ components and corresponding strengths.

In at least some embodiments, the system may further comprise a main sensor to obtain the main signal $Z(n)$ and an auxiliary sensor to obtain the auxiliary signal $Y(n)$.

In at least some embodiments, the processing unit may be further configured to perform at least one embodiment of the general signal estimation methods defined in accordance with the teachings herein.

In at least some embodiments, the processing unit may further be configured to perform Distortion Product Otoacoustic Emission (DPOAE) measurements and the system comprises a first probe having two speakers to provide two stimulus tones to a subject, a main microphone to record the main signal Z(n) and an auxiliary microphone to record the auxiliary signal Y(n).

In at least some embodiments, the processing unit may further be configured to define the at least one signal feature to comprise signal features corresponding to a first stimulus tone, a second stimulus tone, and a DPOAE signal and the noise and interference V(n) and Y(n) components are obtained from the auxiliary signal.

In at least some embodiments, the processing unit may be configured to perform DPOAE suppression measurements, the system comprise a second probe for generating a suppression tone, and the at least one signal feature further comprises signal features corresponding to a tone with a frequency adjacent to the DPOAE tone for noise floor estimation.

In at least some embodiments, the processing unit may be configured to monitor for the occurrence of middle ear muscle reflex (MEMR), by detecting a phase change of a primary tone or intentionally introduced tone between a time period when a suppressor is on and when the suppressor is off, and determining the MEMR occurrence by comparing the phase change to a threshold.

In at least some embodiments, the first probe may comprise a pressure release structure including: a surface channel on a surface of a probe body and beneath an ear tip, the surface channel having a second end coupled to a first portion of an auxiliary channel that leads to the auxiliary microphone; and a second channel having a first end that is coupled to a second portion the auxiliary channel closer to the auxiliary microphone and a second end that is coupled to an external environment of the probe not covered by the ear tip.

In at least some embodiments, the surface channel may have a first end forming a small passage to an ear canal being tested so that ambient noise and any other noise disturbances in the ear canal can be recorded as the auxiliary signal.

In at least some embodiments for audiometric measurements, the system may further comprise a data acquisition unit for generating at least one stimulus to provide to at least one ear of a subject, and collecting response data for an ear under test; and a user Interface to allow an operator to configure the system for performing audiometric tests and displaying the test results.

In at least some embodiments, the processing unit may be configured to perform oscillometric blood pressure monitoring, the system further comprises a blood pressure cuff with conduits for sensing a main pressure and an auxiliary pressure, a main pressure sensor to obtain the main signal Z(n), and a combination sensor having an auxiliary pressure sensor.

In at least some of the blood pressure monitoring embodiments, a first longitudinal edge of the blood pressure cuff comprises a first tube and a second longitudinal edge of the blood pressure cuff comprises a second tube, the tubes being made of material capable of allowing artifacts to be sensed by the auxiliary pressure sensor.

In at least some of the blood pressure monitoring embodiments, the combination sensor may further comprise an accelerometer to obtain the auxiliary signal V(n), the accelerometer being used for sensing physical artifacts during monitoring.

In at least some of the blood pressure monitoring embodiments, the system further comprises a pump and a valve system connected to a bladder of the blood pressure cuff to inflate and deflate the blood pressure cuff during use; and a pressure control unit coupled to the pump and valve system to control the pressure applied to a user during use.

In at least some of the blood pressure monitoring embodiments, the processing unit is further configured to perform at least one of the embodiments of the method for non-invasive blood pressure monitoring.

In at least some of the blood pressure monitoring embodiments, the system may further comprise a data acquisition unit for collecting data from the main sensor and the combination sensor; and a user Interface to allow an operator to configure the system for performing at least one of blood pressure tests and blood pressure monitoring and for displaying the test or monitoring results.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIGS. 8A-8F are structural diagrams of an example embodiment of a DPOAE probe in accordance with the teachings herein.

Figure 1:
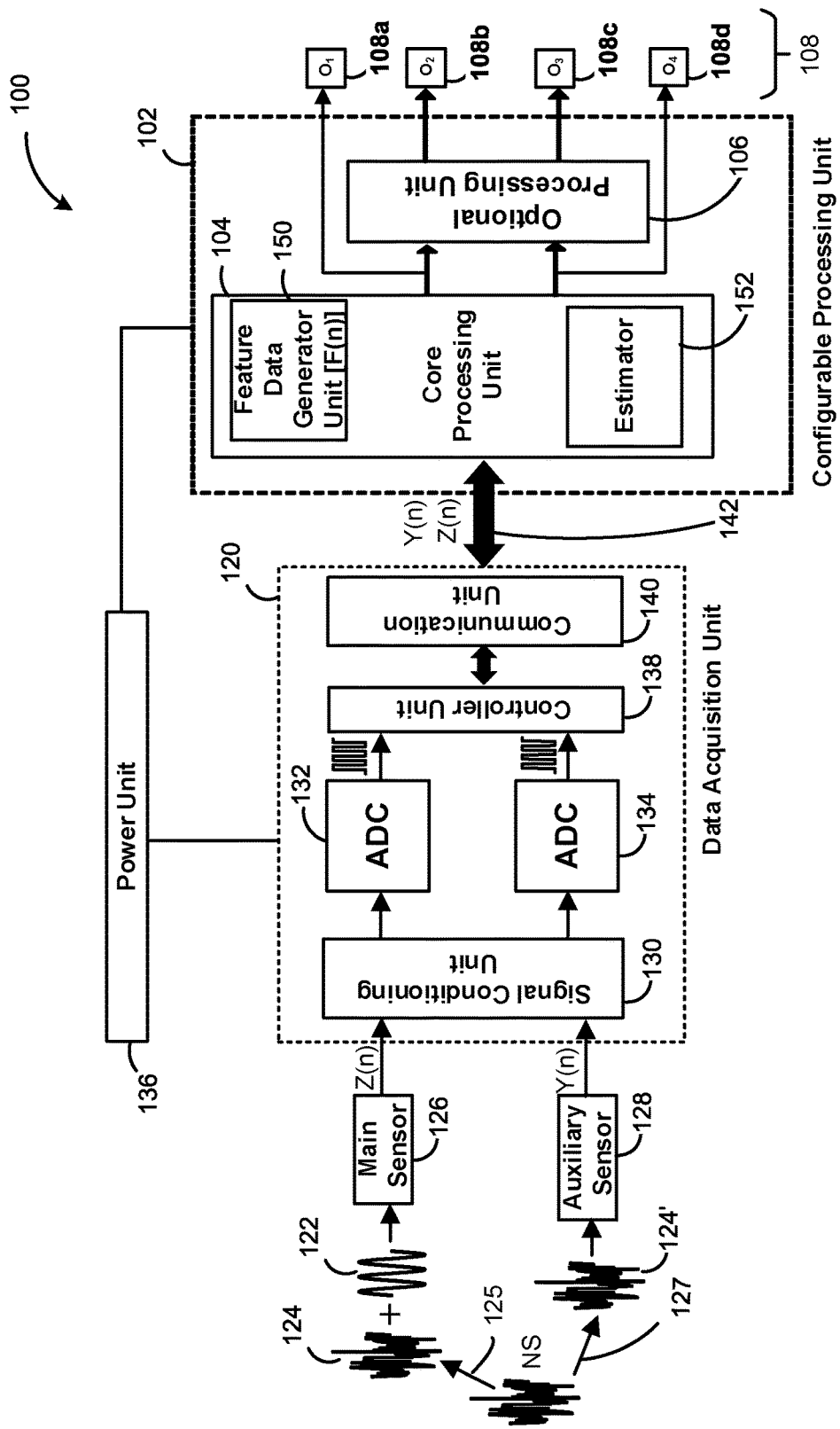
FIG. 1 is a block diagram of an example embodiment of a signal detection system in accordance with the teachings herein.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices and or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 5% or 10%, for example, as the case may be.

The embodiments described herein relate to a system and corresponding devices, transducers and methods for signal acquisition and processing used to addresses the problems associated with detecting a weak signal or a distorted signal due to noise or signal artifacts. The various embodiments of systems corresponding devices, transducers and methods described in accordance with the teachings herein may be applied in various areas including, but not limited to, medical applications such as the field of audiology, neurology and/or cardiology.

In accordance with the teachings herein, various embodiments are described that use adaptive methods for detecting a weak signal or a signal distorted by noise or artifacts, wherein the signal is time-varying. The teachings herein may be applied in various medical applications in which detection of a weak or noisy signal is desired such as, but not limited to: (1) assessing the integrity of the human hearing system from the hearing sensor component (e.g. cochlea) to higher-level neural components by means of Otoacoustic Emission Suppression; (2) measuring blood pressure under significant movement artifacts which contaminate the recorded data and for patients whose pulse may be difficult to detect (e.g. a person with obesity) or those with weak pulses; and (3) monitoring continuously and non-invasively a person's blood pressure with an integrated calibration step.

Referring now to FIG. 1 shown therein is a block diagram of an example embodiment of a signal detection system 100 for detecting a signal in accordance with the teachings herein. The signal detection system 100 comprises a configurable processing unit 102, a data acquisition unit 120, a main sensor 126, an auxiliary sensor 128 and a power unit 136. The configurable processing unit 102 may communicate with the data acquisition unit 120 to obtain signals captured by the main sensor 126 and the auxiliary sensor 128. The power unit 136 may be used to provide power to the data acquisition unit 120, the configurable processor and any other electrical components requiring power.

There are two sensor channels in the signal detection system 100 for sampling data at a desired sampling frequency appropriate for the particular application. The main sensor 126 is used for recording raw data for detecting a desired signal of interest which is signal 122. However, the main sensor 126 may also pick up a noise signal 124 in addition to the desired signal 122. The noise signal 124 comprises unwanted components due to a collective noise source. In practice, there may be several noise sources that produce different types of unwanted components like ambient noise, electrical interference, and artifacts (due to physical activity for physiological recordings) depending on the application at hand but they are considered as a collective noise source NS. Accordingly, the main sensor 126 provides a main signal that comprises the desired signal and unwanted components.

For example, in the present embodiment, the raw data from the main sensor 126 may be defined as $Z(n)=S(n)+V(n)$, where S may be used to denote the desired signal 122, V may be used to denote unwanted components from the noise signal 124 and n may be used to denote the sample or time instant during which a sample is taken. Specifically, $Z(n)$ corresponds to a sample at time instant n of a raw recording from which the desired signal is to be extracted.

Generally, for a single channel recording, Z(n) may be a scalar number. In some embodiments, a multi-channel recording may be implemented such that Z(n) may be a vector with dimension m, where m denotes the number of channels that have been used to measure data.

The auxiliary sensor 128 may be configured to detect an auxiliary signal which is the noise signal 124'. The data from the auxiliary sensor 128 may be defined as the observable interference data Y(n). The noise signal 124' may encompass background noise (i.e. ambient noise), interference, signal artifacts or any other undesired elements which are related to (in other words a version of) the unwanted components in the main signal Z(n) since they may both related to the common collective noise source NS. In general, the degree of noise in the raw data signal Z(n) may not be known. However, information about the collective noise source may be obtained using the auxiliary sensor 128. For example, a noisy environment may comprise a noisy machine (M) running in a room where a person A is talking to person B on a telephone call. In this case, it may be known that the interference source is M, so that a microphone may be mounted in proximity to M to record data that may be used to estimate the machine noise component in the raw recording from person A's microphone. In this case, Y(n) corresponds to the noise recording of noise source M. In some embodiments, there may be multiple sources of noise so that Y(n) may be a vector having several dimensions.

The main signal sensed by the main sensor 126 comprises the desired signal 122 and the noise signal 124, while the auxiliary signal sensed by the auxiliary sensor 128 comprises the noise signal 124'. If the noise signal 124 and the noise signal 124' are from the common collective noise source NS through two linear paths 125 and 127, then the noise signals 124 and 124' are also linearly related to one another. Conceptually, then, both V(n) and Y(n) may be considered to be coupled through a linear system L. Thus, the configurable processing unit 102 may use Y(n) to estimate V(n) so that this noise estimate may be removed from the recorded data Z(n) to improve the SNR of the designed signal 122. Examples of methods for doing so will be described in further detail below.

The configurable processing unit 102 may be used to estimate the desired signal 122 from the main signal Z(n) which has been contaminated with noise or interference and/or other unwanted components. In the present example embodiment, the configurable processing unit 102 may comprise a core processing unit 104 and an optional processing unit 106. The core processing unity 104 may be used to define signal features for the signal and the interference, to estimate the feature strength of the signal components and the feature strength of the interference components, to remove the interference components from the estimation of the desired signal 122 and to reconstruct the desired signal 122. These strength quantities provide weights to each signal feature and each interference component in the raw recorded signal Z(n). As such, these strength quantities may be considered as the magnitudes of each signal feature or interference component.

Accordingly, the core processing unit 102 may also include a feature data generator unit 150 to generate feature data F(n) for the signal features. In other embodiments, the feature data F(n) may be provided by another source, such as a database or another device. The feature data F(n) may be a vector that contains samples of data having prescribed features that may be used as templates for signal estimation and detection. For example, in some embodiments where it is known that the desired signal to be detected within the raw signal Z(n) is a sinusoid with a frequency w then F(n) may be represented by $F(n)=[\cos(\omega n) \sin(\omega n)]^T$. Each element within F(n) is a signal feature. The estimated signal from the raw recording may thus be written as:

$$S(n)=A\cos(\omega n)+B\sin(\omega n) \quad (1)$$

where the coefficient A is denoted as the strength of feature $\cos(\omega n)$ and B is denoted as the strength of feature $\sin(\omega n)$. In general, the signal features along with their strengths combine to produce the desired signal S(n).

The number of dimensions of F(n) depends on the number of features to be detected. In some embodiments, a signal feature does not have to be generated from a closed-form formula as in the example shown above. Rather, the signal features may be generated from a look-up table or an actual recording that has specific characteristics based on the desired signal that is to be detected.

In the example embodiment, the outputs $O_1$ and $O_4$ of the configurable processing unit 102 include the feature strengths 108a and 108d corresponding to the estimated magnitudes of the signal features and the estimated magnitude of the interference components, respectively.

In some embodiments, the configurable processing unit 102 may include the optional processing unit 106 which may be needed when full signal components or noise components are sought such as, for example, in situations where an estimate of both the waveforms and amplitudes of the desired signal S(n) is desired. The optional processing unit 106 may be configured to reconstruct the complete set of components using estimated strengths, inputted features and interference data. The output $O_2$ of the optional processing unit 106 includes reconstructed signal components 108b which corresponds to the estimated waveforms of the signal features seen as components in the raw recording Z(n). The output $O_3$ of the optional processing unit 106 includes reconstructed interference components 108c which correspond to the estimated waveform of the interference components seen in the raw recording Z(n).

Figure 2:
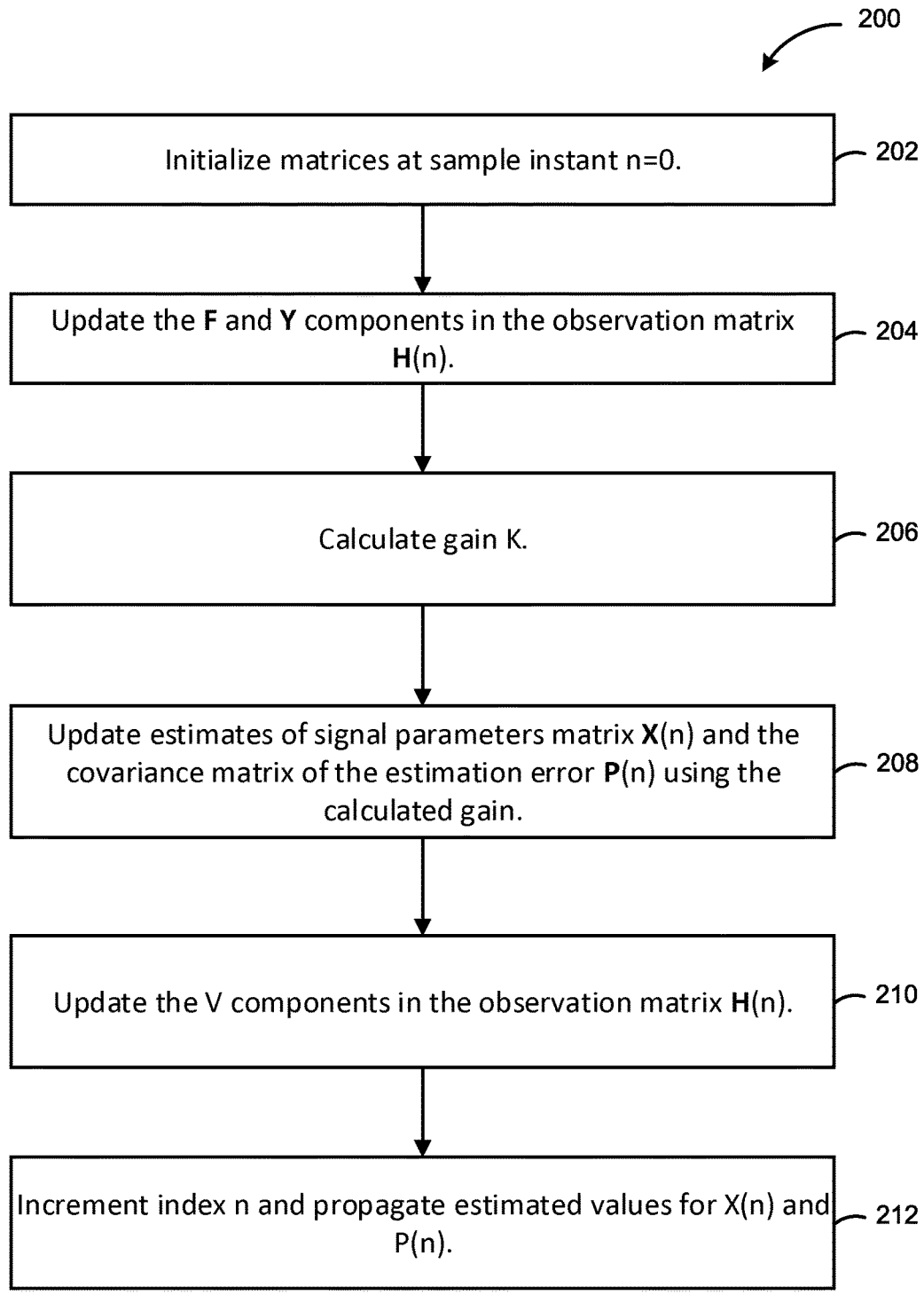
FIG. 2 is a flowchart of an example embodiment of a generalized signal detection method for estimating signal parameters in accordance with the teachings herein.

The configurable processing unit 102 further includes an estimator 152 that is used to provide various estimates needed for the signal and noise modeling used by the system 100 and described in further detail below. The estimator 152 estimates the signal feature strengths and strengths of the interference components. The estimator uses the data Z(n) from the main sensor channel as well as the F(n) from the feature data generator unit 150 in performing the method 200 as shown in FIG. 2 to estimate the signal and the interference strength.

The configurable processing unit 102, the core processing unit 104, the feature data generator 150 and the optional processing unit 106 may be implemented using a high performance general processor, controller or digital signal processor that can provide sufficient processing power as is known by those skilled in the art. In alternative embodiments, these processing units may be implemented using more than one processor with each processor being configured to perform different dedicated tasks. In alternative embodiments, specialized hardware, such as at least one ASIC and/or FPGA, may be used to provide some of the functions provided of these processing units.

The configurable processing unit 102 receives sampled versions of the main and auxiliary signals Z(n) and Y(n) detected by the main sensor 126 and the auxiliary sensor 128, respectively, via the data acquisition unit 120. The data acquisition unit 120 may be powered by a power unit 136, which also supplies power to the internal components such as signal conditioning unit 130 and analog-to-digital converters (ADC) 132 and 134. In some embodiments, the power unit 136 may be a voltage transformer configured to convert alternating current (AC) power to direct current (DC) power. In other embodiments, the power unit 136 may be integrated with the data acquisition unit 120. For example, the power unit 136 may be a battery that is installed into the data acquisition unit 120.

The signals captured by the main sensor 126 and the auxiliary sensor 128 may processed by the signal conditioning unit 130 prior to digitization by the ADCs 132 and 134. For example, the signal conditioning unit 130 may be configured to filter and amplify the recorded signals prior to digitization. The ADCs 132 and 134 may then convert the continuous physical signal to a digital representation that is then sent to the configurable processing unit 102. The type of ADCs 132 and 134 that are used, their sampling resolution and the sampling parameters may depend on the type of application in which the signal detection system 100 is used.

The digitized signals are then sent by the controller unit 138 to the communication unit 140 to transfer the digitized signals to the configurable processing unit 102 via a communications link 142. The controller unit 138 controls the operation of the data acquisition unit 120 and can be any suitable processor, controller or digital signal processor that can provide sufficient processing power as is known by those skilled in the art.

The communication unit 140 may be configured to communicate using any appropriate method known to those skilled in the art. For example, in some embodiments the communication unit 140 may be a wired interface such as a Universal Serial Bus (USB) interface to facilitate wired communication via a USB link to the configurable processing unit 102. In other embodiments the communication unit 140 may facilitate wireless communications. For example, the communication unit 140 may be a Bluetooth interface which establishes a wireless Bluetooth link between the data acquisition unit and the configurable processing unit 102.

Signal and Noise Modeling and Estimation Structure

As described previously, the raw data from the main sensor 126 may be defined as $Z(n)=S(n)+V(n)$, and both the first noise path 125 and the second noise path 127 may be considered to be linear systems. Accordingly, both $V(n)$ and $Y(n)$ may be considered to be coupled through a linear system L. Assuming that L is linear and time-invariant (LTI), then $V(n)$ and $Y(n)$ (the elements related to the noise) can be related using an Autoregressive Moving Average (ARMA) model:

$$v(n)=\sum_{i=1}^{p} a_i v(n-i)+\sum_{i=0}^{q-1} b_i y(n-i)+w(n) \quad (2)$$

where $p$, $q=0, 1, 2, \ldots$ and $w(n)$ is assumed to be zero-mean white Gaussian noise as shown in equation 3.

$$r = E[w(n)w(n-l)] = \begin{cases} \sigma_w^2 & \ldots \text{ for } l = 0 \\ 0 & \ldots \text{ for } l \neq 0 \end{cases} \quad (3)$$

The ARMA model expression may be simplified by first establishing two vectors $X_a$ and $X_b$ with dimensions p and q, respectively, where $X_a=[a_1\ a_2\ \ldots\ a_p]^T$ and $X_b=[b_0\ b_1\ \ldots\ b_{q-1}]^T$ are the ARMA model parameters of the noise components in the main recording Z(n) and the noise components from the auxiliary signal 124', respectively. Secondly the v(n) and y(n) components may be condensed by setting a 1×p matrix V(n−1) in which $V(n-1)=[v(n-1)\ v(n-2)\ \ldots\ v(n-p)]$ and a 1×q matrix Y(n) in which $Y(n)=[y(n)\ y(n-1)\ \ldots\ y(n-q+1)]$. Having made these substitutions, equation 2 above may be re-written as equation 4.

$$v(n)=V(n-1)X_a+Y(n)X_b+w(n) \quad (4)$$

Under real measurement scenarios, the noise and interference paths may vary with time. Therefore, the ARMA model (i.e. equation 2) may be generalized to a time-variant case such that the model parameters may slowly change over time, so that equation 4 may further be rewritten as follows in equation 5.

$$v(n)=V(n-1)X_a(n)+Y(n)X_b(n)+w(n) \quad (5)$$

With respect to the signal, as described earlier, the signal component S(n) in the raw recording Z(n) may be considered a linear combination of the signal features F(n). Therefore, a feature vector with dimensions m×1 may be defined $F(n)=[g_1(n)\ g_2(n)\ \ldots\ g_m(n)]$ where $g_i(n)$ is the time series characterization of feature i of the desired signal S(n). The amplitude/magnitudes or the feature strengths may be denoted by the feature strength vector $X_s(n)=[x_{s1}(n)\ x_{s2}(n)\ \ldots\ x_{sm}(n)]^T$ that corresponds to F(n), where m represents the total number of features in the recorded signal S(n). Therefore the signal component can be written in matrix form as follows in equation 6.

$$s(n)=F(n)X_s(n) \quad (6)$$

Combining all the components together, the raw recorded signal Z(n) obtained from the main sensor 126 of FIG. 1 may be written as:

$$Z(n)=F(n)X_s(n)+V(n-1)X_a(n)+Y(n)X_b(n)+w(n) \quad (7)$$

The raw recorded signal Z(n) may be simplified by establishing a 1×(m+p+q) observation matrix H(n) and a state vector X(n) with (m+p+q) dimensions containing the feature strength and ARMA model parameters, where H(n) and X(n) are defined in equations 8 and 9.

$$H(n) = [F(n) \vdots V(n-1) \vdots Y(n)] \quad (8)$$

$$X(n) = \begin{bmatrix} X_s(n) \\ \ldots \\ X_a(n) \\ \ldots \\ X_b(n) \end{bmatrix} \quad (9)$$

The raw recorded signal from the main sensor 126 can therefore be simplified to the following observation equation z(n):

$$z(n) = H(n)X(n) + w(n) \quad (10)$$

$$r = E[w(n)w(n-l)] = \begin{cases} \sigma_w^2, & \text{if } l = 0 \\ 0, & \text{if } l \neq 0 \end{cases}$$

In some embodiments, the state vector X(n) may be assumed to be a quasi-constant vector such that its change over time is slow compared with the signal feature waveforms or the interference waveforms. Specifically, based on this assumption, the vector may be written as a state equation:

$$X(n)=X(n-1)+u(n-1) \quad (11)$$

where u(n−1) is assumed to be a zero-mean Gaussian white noise vector with dimensions (m+p+q) and further:

$$E[u(n)u(n-l)^T] = \begin{cases} Q & \ldots l = 0 \\ 0 & \ldots l \neq 0 \end{cases} \quad (12a)$$

$$Q = \begin{bmatrix} \sigma_{u1}^2 & 0 & 0 & 0 \\ 0 & \sigma_{u2}^2 & 0 & 0 \\ \vdots & \vdots & \ddots & \vdots \\ 0 & 0 & 0 & \sigma_{u_{m+p+q}}^2 \end{bmatrix} \quad (12b)$$

equations 10 and 11 above may be used to represent a model of the signal detection system 100 of FIG. 1.

Using the concept of a state variable description of a linear system, equation 11 can be considered as a state equation while equation 10 can be considered as an observation equation. A method based on a state variable description of the system, such as Kalman Filtering, may be used to estimate the model parameters. However, equations 10 and 11 are not standard equations that may be used with a Kalman Filter for a number of reasons. Firstly, a standard Kalman filter which takes the form $z_k(n)=H_k(n)X_k(n)+w(n)$ requires that the observation matrix $H_k(n)$ be known and deterministic. However, the observation equation H(n) of equation 10 contains unknown and random variables. Secondly, from equation 8, H(n) comprises three parts, F(n), V(n−1) and Y(n). The matrix F(n) is the feature matrix, which may be defined as described above and thus can be considered as a known quantity. However, in some circumstances, the features may or may not be deterministic because the features of interest may be a random feature. The vector Y(n) can be obtained from the auxiliary sensor 128 and can also be considered as known. Generally, Y(n) may more often be random rather than deterministic. The vector V(n−1) is an unknown quantity (otherwise the noise and interferences can be completely removed from the raw recording) which may pose an obstacle with respect to using Kalman filtering.

Therefore, in consideration of the above limitations, in accordance with the teachings herein, a new procedure is devised that uses a Kalman Filter to estimate the state vector X(n) using the information that is known and information that may be gathered from the signal detection system 100.

The elements of the feature matrix F(n) may be defined on the basis of the desired signal S(n). For example, in some cases, the desired signal S(n) has specific characteristics (e.g. a sinusoid at a given frequency) that may be known ahead of time. For example, in the context of sound waveforms, as described in further detail below, in cases such as distortion product otoacoustic emission detection, the target waveforms are generally known so that features of such waveforms may be established ahead of time. In other cases, when the features in F(n) correspond to a desired signal that is a random process, the realization of that random process may be used to set the F(n) element values. Since a realization of a random process is no longer random at a given point in time, F(n) can be considered to be deterministic for that time.

Secondly, with respect to Y(n), the measurement from the auxiliary sensor 128 may be used to produce the element values of Y(n) since the elements corresponding to Y(n) may be considered to be a realization of a random process. This approach may be particularly useful, as noted previously, since Y(n) is generally more random than deterministic and the sampled value is a realization of this random process. Thus, for a particular measurement, Y(n) can be considered to be deterministic.

Lastly, with respect to V(n−1), it may be assumed that it has an initial condition $V(-1)=V_{-1}$. In some embodiments, the mean of the initial value of V(−1) may be estimated and used as an initial value. On the other hand, if the value cannot be estimated, then an initial value of zero may be used since the estimated V(n) will gradually approach the true value of V(n) in most cases regardless of the initial value V(−1). At a given time point n, an estimate of $X_a(n)$ represented as $\hat{X}_a(n)$ and an estimate of $X_b(n)$ represented as $\hat{X}_b(n)$ can be made using the core processing unit 104. From equation 5, an adaptive approach may be applied in the estimation by ignoring the random term w(n). Additionally, since Y(n) is available from the auxiliary sensor 128, an estimate of V(0), V(1), . . . , V(n) can be made using the recursive equation $v(n)=V(n-1)\hat{X}_a(n)+Y(n)\hat{X}_b(n)$ and V(n)=[v(n), v(n−1), . . . v(n−p+1)].

Using the above procedures, the observation matrix H(n) can be obtained at each sample instant n. In some embodiments, it may be assumed that Q and $\sigma_w^2$, are known (e.g. they can be obtained either experimentally or through adaptive algorithms), so that all the required data for the Kalman Filter methods are available for estimating the signal parameters X(n). For example, $\sigma_w^2$ can be estimated using an adaptive algorithm based on the residue $r(n)=z(n)-H(n)\hat{X}(n)$ where $\hat{X}(n)$ is the estimate of X(n) so that r(n) corresponds to white noise. Similarly Q may be estimated in a similar manner according to Stengel [ref. 4].

Referring now to FIG. 2, shown therein is a flowchart of an example embodiment of a generalized signal detection method 200 for estimating signal feature strengths and noise parameters based on known information and data gathered by the signal detection system 100.

At act 202, the various matrices and vectors defined previously may be initialized at sample instant n=0. For example, the following initialization may be used.

$H(0)=[F(0) \vdots V(-1) \vdots Y(0)]$ $Q=\beta I;$ $r=\sigma_w^2;$ $\hat{X}^-(0)=X_0;$ $V(-1)=0$ $\hat{P}^-(0)=\alpha I, (\alpha \gg 1)$ In the present case, P(n) and P⁻(n) are covariance matrices of the current estimation error and the prior estimation error which may be determined as follows $P(n)=E[(X(n)-\hat{X}(n))(X(n)-\hat{X}(n))^T]$ and $P^-(n)=E[(X(n)-\hat{X}^-(n))(X(n)-\hat{X}^-(n))^T]$ and where $\hat{X}^-(n)$ is a prior estimate of X(n).

In some embodiments, $X_0=0$ and $\hat{P}^-(0)$ is a diagonal matrix in which the diagonal element may be a large number ≫1. The actual value of the number may not be important, as long as the value is large enough. For example, the diagonal elements may be a number (which does not have to be any specific number) that is 10 to 100 times the value of the variance of X(n). The value r can be set to a value equal to the estimated variance of the main sensor recording Z(n) when no desired signal is present (i.e. when the desired signal is a response signal and all stimuli are turned off so there is no response). Q may also be a diagonal matrix, with the diagonal elements all being a small number β. This number can be decided through experiment on simulated or real data. The smaller the value of β, the smoother the estimated signal, but at the expense of a slower speed at which the features can be tracked. Therefore, the choice of β may be decided upon based on acceptable levels of performance with respect to tracking speed and smoothness. Generally, the ratio of β/r may place an effect on tracking speed and estimation smoothness since a smaller ratio results in a narrower Kalman filter bandwidth. In some embodiments, known adaptive algorithms may be applied to optimally estimate Q and r [ref. 4]). Alternatively, in some embodiments, Q=βI may be replaced with a diagonal matrix Q=diag[$β_1$ $β_2$ ... $β_{m+p+q}$] to allow the tracking speed and the smoothness of the estimation for each $x_i(n)$ inside the state vector X(n) to be controlled. Similar to β, the choice of values of may be decided based upon acceptable levels of performance with respect to tracking speed and smoothness through experiments.

At act 204, the F(n), and Y(n) components of the observation matrix H(n) are updated. The update for the signal features may be based on using the feature data generator unit F(n), along with a feature formula (e.g. sine and cosine waves if the desired waveform is a sinusoid), or a table which may be pre-defined or a generated data pattern. In some embodiments, the signals features may be derived from an additional sensor (other than the main and auxiliary sensors 126 and 128) that is dedicated to describing the desired signal S(n). The update for the interference components may be based on data that is collected by the auxiliary sensor 128.

At act 206 a gain K may be calculated based on the relationship:

$$K = \frac{P^-(n)H(n)^T}{H(n)P^-(n)H(n)^T + r} \quad (13)$$

At act 208, estimates of the signal state vector X(n) and the covariance matrix of the estimation error P(n) may be updated using the calculated gain K. Specifically, the estimate of X(n) may be expressed as X(n)=$\hat{X}^-$(n)+K[z(n)−H(n)$\hat{X}^-$(n)] and P(n)=[I−KH(n)]P$^-$(n).

At act 210 the V components of the observation matrix H(n) may be updated. The V(n) components may be updated using the calculation v(n)=V(n−1)$\hat{X}_a$(n)+Y(n)$\hat{X}_b$(n) wherein $\hat{X}_a$(n) and $\hat{X}_b$(n) may be obtained from X(n). In some embodiments of the signal detection system 100, F(n), V(n), and Y(n) may be stored in arrays such as registers and shift-registers. Specifically F(n) may be stored in registers, while V(n) and Y(n) may be stored in shift registers. For example, when new samples of v(n) and y(n) are obtained, they may be shifted to the V and Y arrays respectively. Altogether the F(n), V(n), and Y(n) components form the H(n). It may be appreciated that the various elements may all be updated based on live sensor data. In this view, the Kalman Filtering applied may thus be considered to be adaptive and different from a standard Kalman Filter.

At act 212, the sample time instance n is incremented, e.g., by using n=n+1, and the estimated parameters for X(n) and P(n) are propagated such that $\hat{X}^-$(n)=$\hat{X}$(n−1) and P$^-$(n)=P(n−1)+Q.

It should be noted that in some embodiments the above acts of method 200 may be extended for applications in which there are multiple auxiliary sensor channels. For example, for a signal detection system 100 having i auxiliary channels, additional $Y_i(n)$, $V_i(n)$ components and corresponding $X_{a_i}(n)$ and $X_{b_i}(n)$ may be introduced to H(n) and X(n). In other embodiments, the above acts of method 200 may be extended for applications in which there are multiple main sensor channels. For example, for a signal detection system 100 having j main channels, Z(n) becomes a j-dimensional vector and the observation matrix H(n) has j rows in this case.

The method described above may be considered to be an adaptive Kalman Filter. In contrast, in a standard Kalman Filter, the gain K can be pre-calculated and stored as a look-up table as the model is fully known beforehand and does not rely on real measured data. In this respect, the standard Kalman Filter is not adaptive. However, as described in the preceding paragraphs, some of the components needed for the determination of the signal S(n) become available only as real data is being acquired. In this sense, the procedure and modeling described herein may be said to be an adaptive method.

Furthermore, the signal and noise modeling method described above is also different from standard Kalman filter approach. In the standard Kalman filter approach, the desired signal is modeled through the state equations, and the desired signals are often the elements of the state vectors. In the new methods described here, the desired signals are modeled through the observation matrix H. Although, state equations are still used for determining signal strength, the teachings herein use a computationally efficient and simple state vector equation form as can be seen in equation 11. In general, the state equation has the form X(n)=G(n)X(n−1)+u(n−1) where G(n) is an N×N matrix with N equal to the dimension of X(n). In equation 11, G(n) becomes a unit matrix I. Because of the unit matrix, many calculations in the filter are simplified, and the computation load is reduced. This can be seen by comparing the current method to a general Kalman filter algorithm. In addition, because of this modeling method, the observation matrix H(n), which contains V(n), becomes dependent on g(n) and act 210 is added to the processing as shown in FIG. 2. In conventional observation matrices, H(n) does not dependent on $\hat{X}$(n) and the Kalman filtering does not conventionally employ step 210. So to avoid the possible confusion in terminology, method described in accordance with the teachings herein may be referred to as a quasi-Kalman filter.

Described in the subsequent sections are example embodiments of using the configurable system and method described above for various medical applications in which detection of a weak desired signal or detection of a desired signal with contamination is desired. However, it should be understood that the specific examples that will be discussed are given by way of illustration only and not by way of limitation. Various substitutions, modifications, additions, and/or rearrangements of the embodiments described herein will become apparent to those skilled in the art from this disclosure.

Example 1: Distortion Product Otoaucoustic Emission (DPOAE) Suppression Detection The hearing system comprises a sensory part and a neural processing part. In current clinical practice, the integrity of the sensory part of an individual's hearing system may be assessed by mechanical (e.g. bioacoustical) means while the neural part of an individual's hearing system may be assessed by electrical (e.g. bioelectrical) means.

One way to assess an auditory sensor (e.g. the cochlea) is to detect a Distortion Product Otoacoustic Emission (DPOAE) from the ear. The DPOAE is a low level sound generated from the inner ear (i.e. cochlea) as a response to two stimuli, called primaries, each comprising a pure tone at a given frequency. The presence or absence of the DPOAE may be used as an indicator of whether the sensor (e.g. outer hair cells in the cochlea) is functioning. This method has been widely used in clinical settings for diagnosis and hearing screening.

In general, during a standard DPOAE test, a probe with built-in speakers and microphones may be inserted into the subject's ear canal. Two pure tones with frequencies f1 and f2 are sent to the subject's ear. An ear with normal functionality generates a tone at frequency 2f1-f2 called the DPOAE. The goal of the DPOAE test is to measure and detect the DPOAE generated by the ear being tested.

Diagnostic information provided by a standard DPOAE recording (i.e. acoustical recording) may be limited as it can only give information of the hearing system from the outer ear up to the cochlea. Where information regarding higher level auditory processing (i.e. neural processing) is desired, electrical recordings such as an electroencephalogram (EEG), particularly an Auditory-evoked Brainstem Response (ABR), which is an Auditory Evoked Potentials, may have to be used.

It is generally known that during a DPOAE test, an extra stimulus (e.g. a third tone or a wide-band/narrow-band noise signal) is applied other than the standard primaries to the ear not being tested (e.g. contralateral ear) to induce a change to the DPOAE emitted by the ear that is being tested. The change is normally a decrease in the DPOAE sound level, which is a phenomenon known as DPOAE Suppression. The goal of DPOAE suppression test is to measure and detect this change in sound level due to the additional contralateral stimulus. Experimental evidence shows that the changes are caused by neural modulation in the neural processing part of the subject's hearing system. By measuring the changes due to DPOAE suppression, one may obtain information regarding the subject's auditory sensor and auditory nerves involved in the testing. In other words, from a single acoustical recording alone, it may be possible to assess the integrity of both the sensory and neural parts of an individual's hearing system.

There are generally two methods for DPOAE detection, one is based on using the FFT and frequency domain averaging and the other is based on time domain narrow band filtering. Time domain filtering allows real-time detection of DPOAE suppression. Adrian L, James et al. [ref 1] have demonstrated the advantages of the real-time DPOAE suppression measurement and suggested that it may provide a new tool to diagnose a broader hearing system through a quick acoustic-only test. However, the real-time DPOAE Suppression can only conventionally be reliably recorded in animals, quiet neonates or young subjects using the current conventional methods. However, it may take a much longer amount of time to obtain a stable measurement when artifacts are present, for example, if the subject is an "unquiet" baby. Furthermore, it is also known that the detectability of real-time DPOAE Suppression degrades as a function of the subject's age. For example, Konomi et al. [ref. 2, FIG. 2] reports that DPOAE detection rate decreases as the subject's age increases, from about 95% in neonates down to only about 18.2% in adults aged 41 or above. As such, the current known conventional systems and methods used for DPOAE suppression may provide only limited clinical usability.

Yet another problem associated with DPOAE suppression testing is that multiple neural paths can cause DPOAE suppression as reported by Wolter et al. [ref. 3]. Particularly, a loud sound presented to one ear may trigger a middle ear muscle reflex (MEMR) which stiffens the tympanic membrane of both ears making sound transmission between the middle ear and the outer ear less efficient, thereby causing a reduction of DPOAE amplitude. In a DPOAE test, the suppression of interest is the one mediated by the medial olivocochlear system (MOOS) rather than the one mediated by the MEMR. Under research environments, the MEMR effects on DPOAE suppression may be controlled by using only low level suppression stimuli. However, in the clinical setting, it may be necessary to develop an easy-to-use method that can monitor the effects of MEMR-induced DPOAE suppression and separate MEMR-induced DPOAE suppression from MOCS-induced DPOAE suppression.

In addition, it should be noted that the testing speed and the detectability of the DPOAE suppression is highly dependent on the SNR of the DPOAE recording. To increase the SNR, it is desirable to enhance the signal and reduce the noise (or interference) in the recorded data.

To enhance the signal, it may be desirable that the transmission path from the signal generator to the sensor has a minimal signal loss. For DPOAE testing, it is known that the signal generator is inside the cochlea of the inner ear. The generated sound (i.e. the DPOAE) is first coupled to the auditory bone structures in the middle ear and causes the eardrum (i.e. tympanic membrane), which is attached to the auditory bones and separates the middle ear and ear canal, to vibrate and transmit the sound to the outer ear canal. A DPOAE acoustic probe which comprises a microphone may be fitted in the outer ear canal and used to sense this very faint sound. It should also be noted that the stimuli used to elicit the DPOAE uses the same anatomical pathway to transmit sound, only in the reverse direction, in order to travel towards the tympanic membrane. The status of the tympanic membrane can thus significantly affect the efficiency of the sound transmission. It is generally considered optimal when the pressure between the outer ear and the middle ear is in balance. In accordance with the teachings herein, a pressure relief structure, described in further detail below, may be used to prevent static pressure from being built-up in the ear canal when the DPOAE probe is inserted to the ear canal. In addition to the pressure relief, a portion of this structure may also be used as a sensing channel for improving the SNR.

To reduce noise or interference from contaminating the DPOAE recording, narrowband filters may be used. The narrower the filter's pass band, the better the noise reduction. However, when the bandwidth is too narrow, the filter may lose its ability to track DPOAE changes quickly and accurately. In general, for a given tracking speed, the bandwidth of the passband may be determined based on the SNR of the recorded signal such that the bandwidth is narrowed until an acceptable SNR is reached. But for some noisy data, acceptable SNR may not be achievable for a given tracking speed. Therefore, a method of noise reduction other than simply deceasing the filter's bandwidth is desirable. To determine an efficient noise reduction method, an analysis of the noise sources may be done.

It is generally known that there are at least two major sources of noise/interference in a DPOAE recording. A first noise source is the ambient noise/interference and a second noise source relates to noise/interference in the occluded ear canal caused by the subject's movement, as well as by the subject's blood flow pulsation or other physiological activities. The second noise source normally has most of its energy concentrated in the low frequency spectrum region (e.g. in the 10 Hz range), but a small portion of that energy may extend to a higher frequency region.

Since the DPOAE suppression signal is much smaller in amplitude and covers a wider frequency region compared with the baseline DPOAE signal, the suppression signal may therefore be sensitive to even smaller levels of interference energy. As will be described in more detail below, a DPOAE probe with an auxiliary microphone may be connected to a specially designed ear pressure release structure of the DPOAE probe to sense the ambient noise and the ear canal noise simultaneously. The signal generated by the auxiliary microphone may then be processed to model and remove both the ambient and ear canal noise/interference components in the main microphone recording.

In addition to tracking changes the DPOAE levels, the signal processing methods described in accordance with the teachings herein may also be used to track phase changes of the DPOAE as well as the stimulus tones. Based on the observed phase changes, a method for detecting the Middle Ear Muscle Reflex (MEMR) may be developed in accordance with the teachings herein. The MEMR is also known as the Auditory Reflex, which plays an important role in DPOAE suppression testing (as previously described) and has significant clinical value. It is a protection mechanism of the hearing system. The tympanic membrane will be driven to a stiffer state when loud sounds are presented in either ear to attenuate the sound passing through it. As a result, a stiffer tympanic membrane can reduce the potential damage suffered by the inner hair cells.

Figure 3:
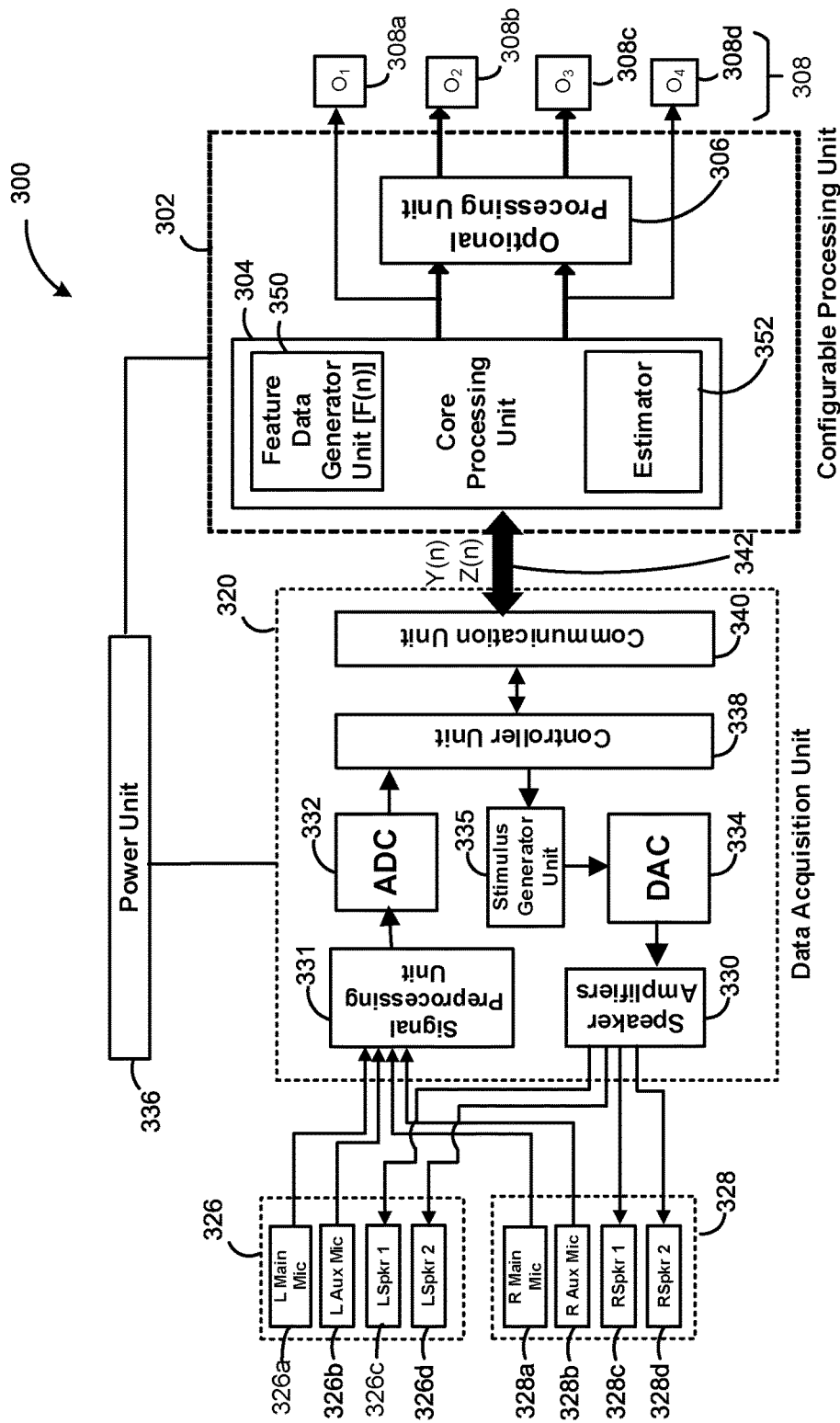
FIG. 3 is a block diagram of an example embodiment of a Distortion Product Otoacoustic Emission (DPOAE) suppression detection system in accordance with the teachings herein.

Referring now to FIG. 3, shown therein is a block diagram of an example embodiment of a DPOAE suppression detection system 300 in accordance with the teachings herein. Similar to the signal detection system 100, the DPOAE suppression detection system 300 comprises a configuration processing unit 302, a data acquisition unit 320, a power unit 336, and a main sensor 326 and an auxiliary sensor 328. Components that are common to both systems 100 and 300 perform similar functions as previously described.

In the present embodiment, the core processing unit 304 may be configured to implement digital signal processing (DSP) algorithms and the data acquisition unit 320 may be optimized to obtain and pre-process data for those algorithms. For example, using adaptive ARMA and time-variant state equation modeling of the DPOAE and the interference/noise signals, optimal DPOAE estimation methods may be developed. Furthermore, experiments on simulated and real recordings may be used to fine tune the system to improve testing speed and detection sensitivity at low SNR conditions. In at least some embodiments, in addition to tracking the changes in the DPOAE level, the method may also be used to track the phase changes of the DPOAE as well as the stimuli tones. Based on the amplitude and phase changes, methods for monitoring the MEMR may be developed.

It should be noted that the new DPOAE and MEMR detection methods described herein are not limited to sinusoidal type stimuli and contralateral stimulation. The methods may be extended to other types of OAEs, for example Transient-Evoked Otoacoustic Emissions (TEOAEs), and may be used for ipsilateral probe configuration.

The DPOAE suppression detection system 300 also includes a left DPOAE probe 326 and a right DPOAE probe 328 designed to be inserted into the subject's left and right ear, respectively. The probe 326 comprises first second speakers 326c and 326d and the second probe 328 comprises first and second speakers 328c and 328d which may be used to generate the DPOAE inducing tones (i.e. the primaries). The probes 326 and 328 also comprise a main microphone 326a and 328a, respectively, which are configured to receive the DPOAE signal during testing. The probes 326 and 328 also comprise an auxiliary microphone 326b and 328b, respectively, which may be used to determine interference and noise as discussed above.

Tones for eliciting the DPOAE may be selected by providing an appropriate command to the controller unit 338. For example, the commands to the controller unit 338 may indicate the frequencies of the two primary tones desired by a clinician, the volume of the tones and their durations. For example, the primary tones may range between 50-70 dB SPL in clinical settings. The stimulus generator unit 335 receives stimulus control instructions and a trigger signal from the controller unit 338 to begin generating the stimuli with the desired parameters. The output of the stimulus generator unit 335 is converted into an analog waveform by the digital-to-analog converter (DAC) 334 whose output is amplified by the speaker amplifiers 330. The output of the speaker amplifiers 330 drive the first and second speakers 326c, 326d, 328c and 328d so as to produce the desired tone in the ear canals of an individual being tested using DPOAEs, in this example. It may be appreciated that in some embodiments, the stimulus generator unit 335 is an analog signal generator configured to directly output an analog signal so that the DAC 334 is not required. In other embodiments, the stimulus generator unit 335 may also perform signal amplification such that a separate speaker amplifier 330 is not required.

During audiometric testing, DPOAE signals are detected by the main microphones 326a and/or 328a. These microphones may also be used to detect tones corresponding to the primaries used to elicit the DPOAE signal as well as noise and interference. Concurrently, noise and interference signals are detected by the auxiliary microphones 326b and/or 328b. The outputs of the microphones 362a and 362b and/or the microphones 328a and 328b are processed by the signal preprocessing unit 331 (i.e. for signal conditioning) and then digitized by the ADC 332 before being forwarded to the communication unit 340 by the controller unit 338. The communications unit 340 then sends the digitized signals via the communications link 342 to the core processing unit 304 for processing.

In the present embodiment, the DPOAE probes 326 and 328 may be used concurrently for DPOAE suppression testing. For example, for DPOAE suppression testing of the left ear, the left DPOAE probe 326 may be used to generate the necessary primaries to elicit a DPOAE signal from the left ear while the right ear may be used to produce the desired stimulus in the right ear to induce suppression of the DPOAE generated by the left ear.

Figure 4:
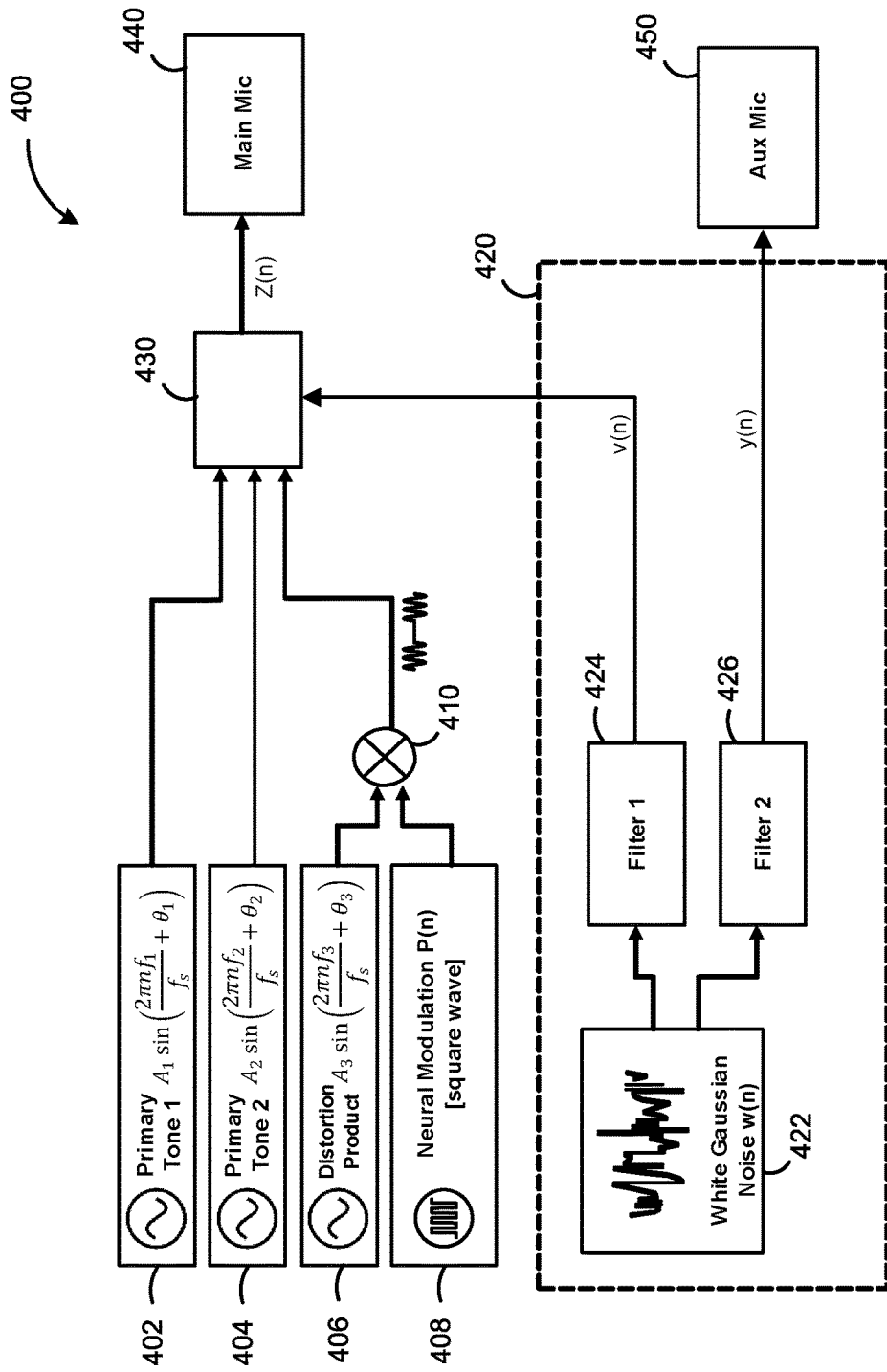
FIG. 4 is a block diagram of an example embodiment of a simulated DPOAE signal generator in accordance with the teachings herein.
Figure 5A:
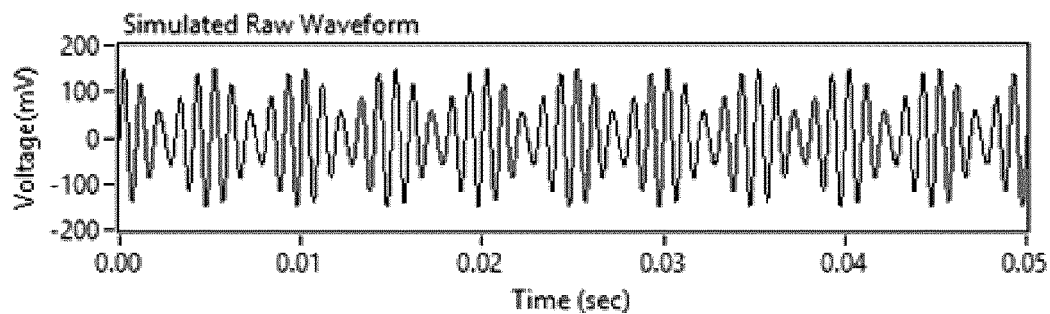
FIGS. 5A-5C depict waveforms of a simulation of a DPOAE suppression detection system in accordance with the teachings herein.
Figure 5B:
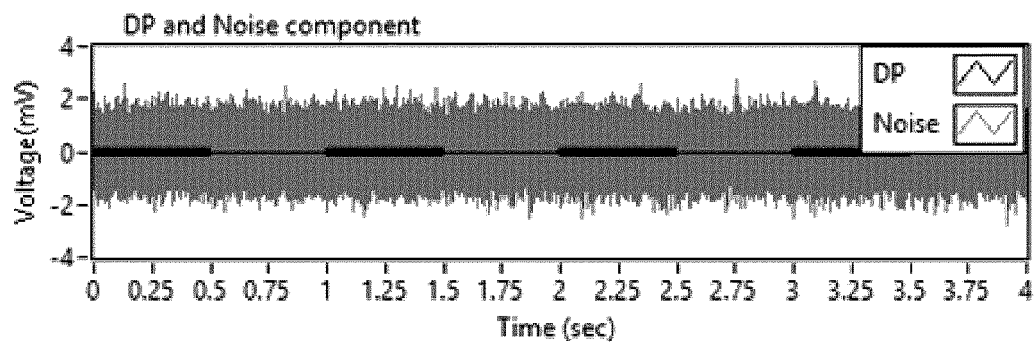

Referring now to FIG. 4, shown therein is a block diagram an example embodiment of a system 400 in which a simulated DPOAE suppression signal may be generated to facilitate the determination of hardware parameters for the system 300 that may be used during actual testing with subjects, and to facilitate the testing of the signal detection methods described herein. The first primary tone generator 402 and the second primary tone generator 404 may be configured to generate a first tone having a desired frequency $f_1$ with a first amplitude $A_1$ and to generate a second tone having a desired frequency $f_2$ with a second amplitude $A_2$. A third tone generator 406 may be configured to generate the expected distortion product at a third frequency $f3=2f_1-f_2$ having an amplitude A3 as shown in FIG. 5B. A square wave generator 408 may be configured to produce a neural modulation signal at a desired frequency $f_4$ to simulate DPOAE suppression. In some embodiments, the frequency may range between 0.25 to 1 Hz, corresponding to a modulation signal period of 1 to 4 seconds. The output of the square wave generator 408 and the third tone generator 406 may then be combined by a mixer 410 to simulate DPOAE suppression.

At the same time, a noise generation block 420 may be configured to produce a simulated noise/interference signal. The noise generation block 420 may comprise a white Gaussian noise source 422 which may simulate a common collective noise source for both the main and auxiliary microphone channels. The output of the white Gaussian noise source 422 may be configured to produce two noise outputs, one for the main microphone 440 and another for the auxiliary microphone 450. The noise to be transmitted to the main microphone 440 may be filtered through a first filter 424, while the noise to be transmitted to the auxiliary microphone 450 may be filtered by a second filter 426. In the present embodiment, the filters are band-pass filters which may be used to simulate the noise coupling paths, such as those indicated by reference numerals 125 and 127 in FIG. 1, which ambient noise may pass through. The output of the first filter 424 as shown in FIG. 5B may be denoted as V(n), which is the noise signal described previously for system 100. In some embodiments, the filters 424 and 426 may be configurable digital filters such as infinite impulse response filters.

Figure 5C:
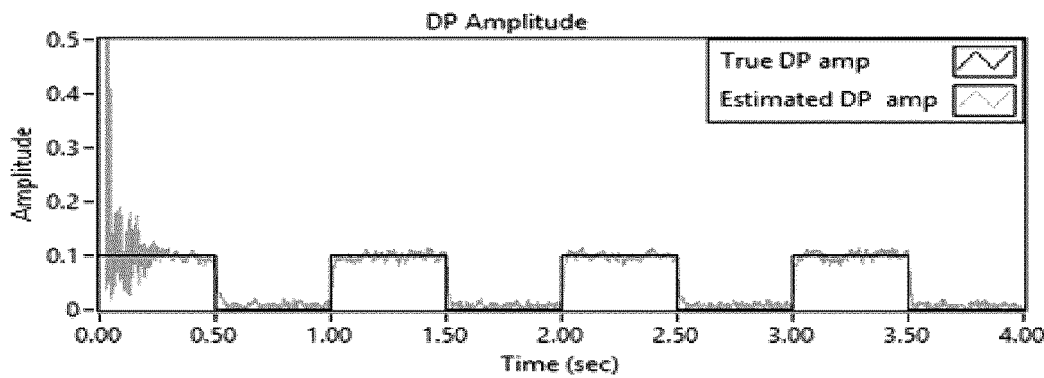

The signal V(n) along with the primaries generated by the first tone generator 402 and the second tone generator 404 and the DPOAE suppression signal at the output of the mixer 410 may be combined by the summer 430 which produces a simulated main microphone signal Z(n) as described previously for system 100 and as shown in FIG. 5A. The noise detected by the auxiliary microphone 450 may be denoted as Y(n) using the same naming convention as described above for system 100. FIG. 5C shows an example of the estimated (i.e. recovered) DPOAE amplitude based on the simulated DPOAE suppression data, in accordance to the methods described in further detail below. The simulations indicate that to optimize processing of the detected signals, the transfer functions corresponding to the auxiliary microphone channel should match the transfer function of the main microphone channel as closely as possible. In some instances the design of the probe and microphone amplifiers may be adjusted to optimize the matching between the main and auxiliary microphone channels.

To determine the amplitude of the DPOAE suppression signal the general methodology described previously in method 200 may be applied. For example, in the present example embodiment, Z(n) may be set to be the signal obtained from the main microphone 326a or 328a (depending on the ear being tested) at a sample instance n. The quantity Y(n) may be set as the signal obtained from the auxiliary microphone 326b or 328b (corresponding to which main microphone is being used) at the same sample instance n. The quantity V(n) may represent the interference or noise that is coupled to the main microphone 326a or 328a. As described previously, the following representations may be used: $Y(n)=[y(n)\ y(n-1)\ \ldots\ y(n-q+1)]$ which is a 1×q matrix and $V(n-1)=[v(n-1)\ v(n-2)\ \ldots\ v(n\ p)]$ which is a 1×p matrix.

For DPOAE suppression testing, the signal components of the primaries as well as the DPOAE signal may be used to define the features in the feature matrix F(n) as follows:

$$F(n)=[\cos(\omega_1 n)\sin(\omega_1 n)\cos(\omega_2 n)\sin(\omega_2 n)\cos(\omega_3 n)\sin(\omega_3 n)\cos(\omega_4 n)\sin(\omega_4 n)] \quad (14)$$

where $$\omega_k = \frac{2\pi f_k}{f_s},$$

k=1, 2, 3, 4; $f_s$ is the sampling rate of the ADC 332; $f_1$ is the frequency of first tone of the primary; $f_2$ is the frequency of the second tone of the primary; $f_3=2f_1-f_2$ is the DPOAE frequency; $f_4=\alpha f_3$ represents the noise floor estimation in which $\alpha\approx1$, e.g =1.1 for DPOAE measurements. These values together may be used to define the observation matrix $H(n)=[F(n) \vdots V(n-1) \vdots Y(n)]$.

The signal strengths or amplitudes of the features (i.e. the elements of feature matrix F (n)) may be defined as $x_{sc1}(n)$, $x_{ss1}(n)$, $x_{sc2}(n)$, $x_{ss2}(n)$, $x_{sc3}(n)$, $x_{ss3}s(n)$, $x_{sc4}(n)$ and $x_{ss4}(n)$. Thus, $X_s(n)$ (of equation 9 above) may be defined as $Xs(n)=[x_{sc1}(n),\ x_{ss1}(n),\ x_{sc2}(n),\ x_{ss2}(n),\ x_{sc3}(n),\ x_{ss3}s(n),\ x_{sc4}(n)\ x_{ss4}(n)]^T$.

The interference strengths (i.e. the autoregressive coefficients) of the corresponding interference terms v(n-1) v(n-2) ... v(n-p) in the main signal recording may be defined as $a_1(n)\ a_2(n)\ \ldots\ a_p(n)$. Additionally, the interference strengths (i.e. the moving average coefficients) of the corresponding interference terms y(n) y(n-1) y(n-q+1) in the auxiliary signal recording may be defined as $b_0(n)\ b_1(n)\ \ldots\ b_{q-1}(n)$. Furthermore, $X_a$ may be defined as $X_a(n)=[a_1(n)\ a_2(n)\ \ldots\ a_p(n)]^T$ and $X_b$ may be defined as $X_b(n)=[b_0(n)\ b_1(n)\ \ldots\ b_{q-1}(n)]^T$ so that vector X(n) may be $X(n)=[Xs(n) \vdots X_a(n-1) \vdots X_b(n)]^T$.

With these definitions established, the method 200 of FIG. 2 may be applied to estimate the primaries and the DPOAE in real-time from the signal Z(n) captured by the main microphone.

In the present example embodiment, the waveform DP(n) of the distortion product (DP) may be determined by equation 15a.

$$DP(n)=x_{sc3}(n)\cos(\omega_3 n)+x_{ss3}(n)\sin(\omega_3 n) \quad (15a)$$

Based on the above expression for DP(n), the magnitude of the distortion product $DP_{amp}$ (n) may be determined by equation 15b.

$$DP_{amp}(n)=\sqrt{[x_{sc3}(n)]^2+[x_{ss3}(n)]^2} \quad (15b)$$

The phase of the DP phase may be determined by equation 15c.

$$DP_{phase}(n) = \tan^{-1}\left(\frac{x_{ss3}(n)}{x_{sc3}(n)}\right) \quad (15c)$$

The other signal components such as the primary tones may be obtained in a similar manner.

Since the phase change of both the primary tones and the DPOAE can be estimated in real-time using the method described herein, a method specifically for monitoring the middle ear muscle reflex (MEMR) in real-time during the DPOAE suppression test may also be developed. For example, when a loud suppressor sound is presented to the contralateral ear canal, the middle ear muscles may drive the tympanic membrane of both ears to a stiffer state. During DPOAE testing, the primary tone stimuli generated by the speakers of the DPOAE probe first travel forward to the tympanic membrane. When the stimuli arrive at the tympanic membrane, they are separated into two parts: a transmitted part which passes through the tympanic membrane and propagates to the middle ear and a reflected part which is reflected by the tympanic membrane back to the microphone. The forward wave and the backward wave of the reflected part may be summed at the main microphone. The relative magnitude changes between the forward and backward waves may cause a phase change of the primary tones recorded by the main microphone. When the MEMR occurs, due to using loud stimuli for eliciting DPOAE suppression, the stiffness of the tympanic membrane may suddenly increase, which causes a sudden increase of the reflected wave that may lead to a sudden change in the detected primary tone phase. Since the primary tones are high level signals, about 50-70 dB SPL, their amplitude and phase can be reliably measured in real-time with the method described herein. By monitoring the primary tone phase change, the occurrence of the MEMR may be detected.

At a higher frequency, the membrane response and the sound waves in the ear canal become more complicated. To use the above signal estimation method, a low frequency tone (e.g. at 10-30% of the DPOAE frequency) in the DPOAE probe may be introduced for MEMR monitoring, rather than using high frequency primary tones as long as the introduced tone does not cause an observable DPOAE response change.

Data Acquisition Hardware for DPOAE Suppression Detection

Figure 6:
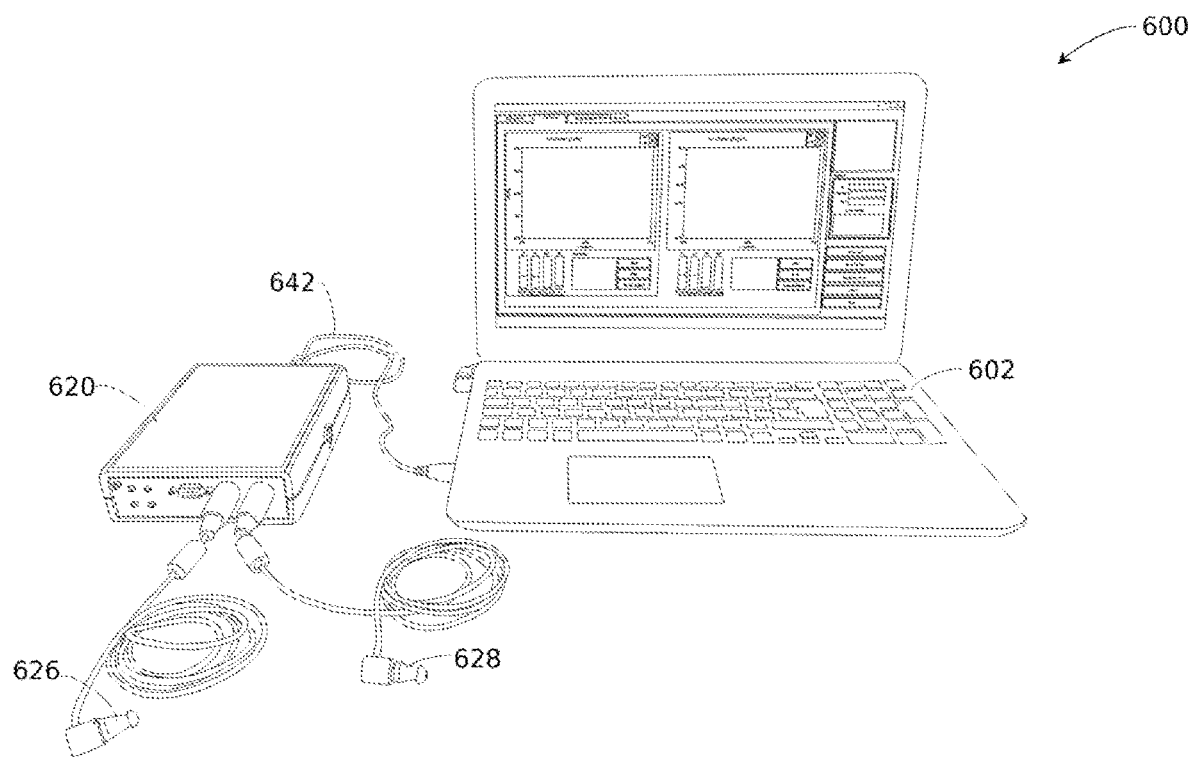
FIG. 6 shows another example embodiment of a DPOAE suppression detection system in accordance with the teachings herein.

Referring now to FIG. 6, shown therein is another example embodiment of a DPOAE suppression detection system 600 that corresponds to the system 300 of FIG. 3. Accordingly, similar numbering is applied in correspondence to the component modules of FIG. 3. In the present example embodiment, the configurable processing unit 602 may be a computer such as a laptop computer. However, it would be appreciated that other configurations or combinations of hardware or software may be used. For example, in other embodiments, the configurable processing unit 602 may be a handheld computing device such as a tablet, a mobile phone or a wearable computing device. The data acquisition unit 620 as shown in FIG. 6 may be connected to the configurable processing unit 602 via a data cable 642 to provide a communications link to facilitate data transfer between the data acquisition unit 620 and the configurable processing unit 602. The data cable may be a USB cable or another wired communications link. However, in other embodiments a wireless communications link may be established instead using wireless communication protocols known in the art such as Bluetooth.

Attached to the data acquisition unit 620 are two DPOAE probes 626 and 628, which may be identical and may be configured in a manner similar to those described in FIG. 3. Each probe 626 and 628 may be used as a standard DPOAE probe for providing the DPOAE stimuli and recording the resulting DPOAE or as an insert phone for (i.e. a DPOAE probe that is configured to only produce an output sound) presenting the DPOAE suppression stimuli (i.e. the suppressor). Whether the probes 626 and 628 are used as a DPOAE probe or as a suppressor insert phone may be fully controlled by the data acquisition unit 620, via commands received from the configurable processing unit 602. For example, a clinician may specify the ear in which the DPOAE suppression is to be measured, and the appropriate probe is chosen to be the DPOAE probe and while the other probe is configured as the suppressor insert phone.

Figure 7:
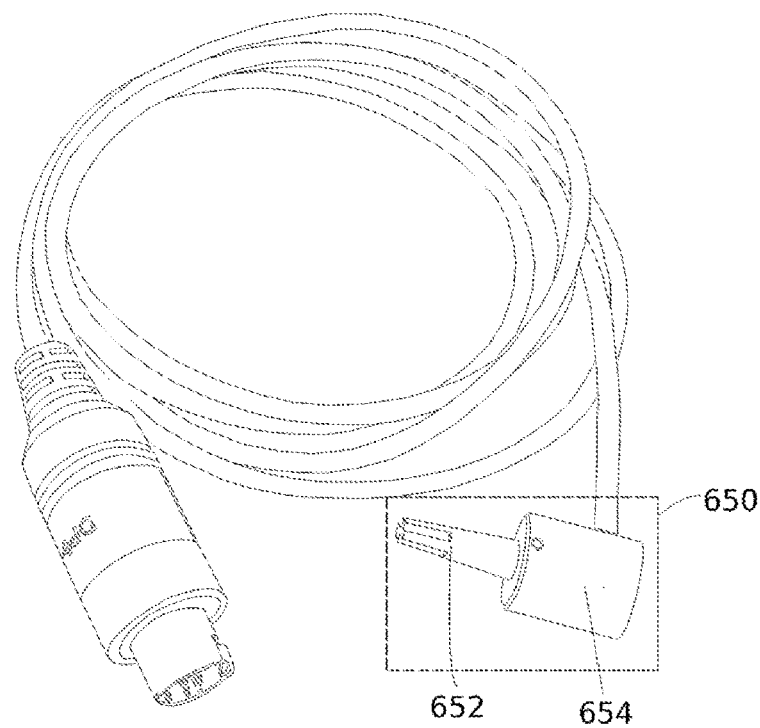
FIG. 7 shows of an example embodiment of a DPOAE probe in accordance with the teachings herein.

Referring now to FIG. 7, shown therein is an example embodiment of a DPOAE probe 650 in accordance with the teachings herein. As shown by the dashed box, the DPOAE probe 650 may comprise a narrow conical insert 652 to fit into the ear canal and a wider cylindrical portion 654 to house the necessary electronics for proper operation of the DPOAE probe 650 during use. The probe material used to make the DPOAE probe 650 may be made using a variety of biocompatible materials such as plastic or other materials as is known by those skilled in the art.

Figure 8D:
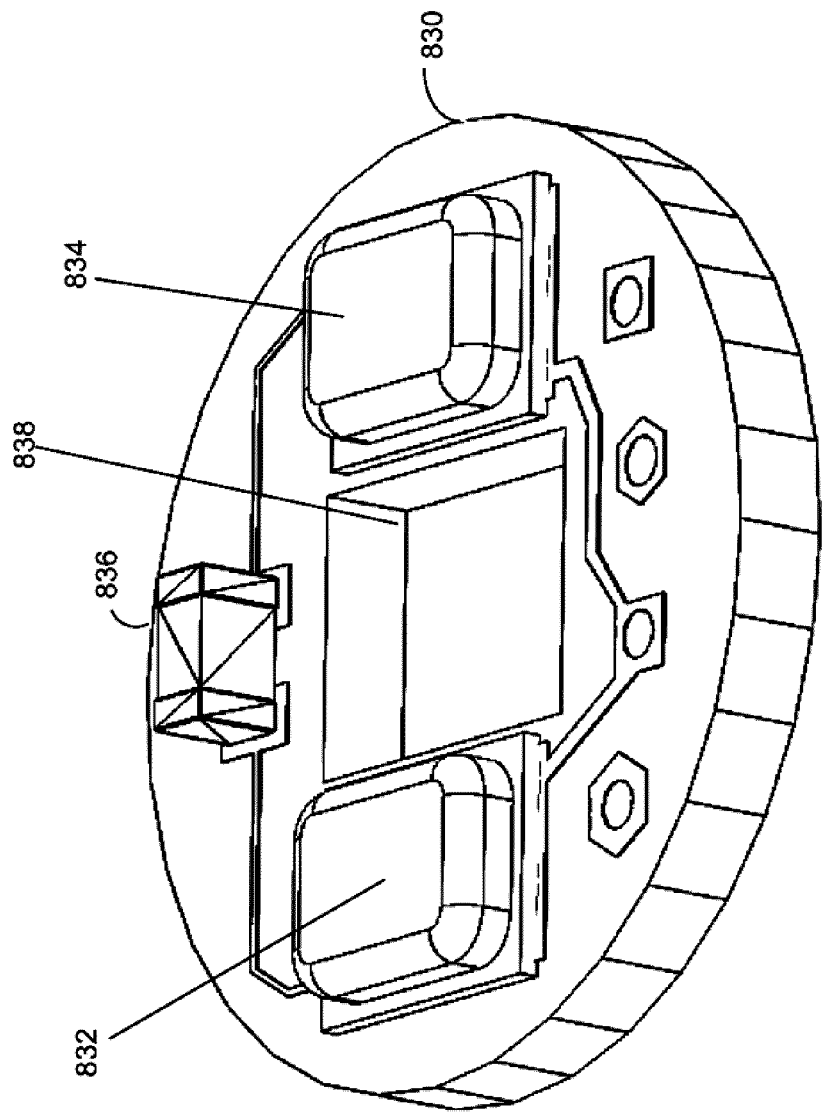

Referring now to FIGS. 8A-8E, shown therein are structural diagrams of the various components of an example embodiment of a DPOAE probe 800 that is similar to the DPOAE probe 650. FIG. 8A is an exploded perspective view of the DPOAE probe 800. A large cylindrical probe cap 802 may be used to house two probe speakers 850a and 850b which may be configured to generate the primary tones ($f_1$ and $f_2$) needed to generate a DPOAE stimulus signal when the probe 800 is used as a DPOAE probe and generate a suppressor signal when the probe 800 is used as a suppressor insert phone. A cable hole 803 is disposed at the probe cap 802 to accommodate a cable for providing connectivity between the DPOAE probe and the data acquisition unit 620. A latch pin hole 803' may be present to provide insertion of a latch pin to a corresponding latch pin hole on the probe housing 804 to secure the probe cap 802 to the probe housing 804. A printed circuit board (PCB) 830 may be used to accommodate the main microphone 832 and auxiliary microphone 834 (also see FIG. 8D). A pliable ear tip 824 with an enlarged distal portion 825 releasably engages the distal portion of the probe body 806.

The PCB 830 and the speakers 850a and 850b may be enclosed in the probe housing 804 which is releasably engaged by the probe cap 802 to assemble the probe 800. For example, probe latch pins 820 and 822 may be used to hold the probe cap 802 and the probe housing 804. The latch pins 820 and 822 may be made of metal, plastic or other suitable materials. In this example embodiment, the hole 821 inside the pin 820 is sealed at the other end (e.g., see FIG. 8F). However, in some embodiments the hole 823 inside pin 822 is open for pressure release and noise/interference sensing as is described below.

The probe body 806 may be tapered to fit into the ear canal, and may comprise a number of longitudinal channels 815, 816, 818 and 819 along the surface of the distal end of the probe body 806 (i.e. closest to the tympanic membrane when inserted into a person's ear). It may be appreciated that when the probe 800 and the soft ear tip 824 are inserted into the subject's ear channel, no air passage is available from the ear canal (enclosed by the probe and tympanic membrane) to the environment external to the ear if the channel 815 was blocked, for example, by ear wax. But the channel 815 is disposed on the surface of the probe body 806, so that when the ear tip 824 is taken off the channel 815 is exposed and can easily be cleaned to prevent it from being blocked. This makes channel 815 an important part of the pressure release path. The channels 816 and 819 may be used to deliver sound to the ear channel. The channel 818 may be coupled to the main microphone 832 while the channel 817 may be coupled to the auxiliary microphone 834. Since the auxiliary microphone 834 does not need to capture the DPOAE signal, the channel 817 is sealed at the tip side of the probe 800 when the probe 800 is fully assembled. However, the channel 817 is coupled to a small hole 823 inside the latch pin 822 to form a passage to the external environment. The channel 817 is also coupled to the small surface channel 815 through hole 814' to form a small passage to the testing ear canal so that ambient noise and any other noise disturbances in the ear canal can be recorded as the auxiliary signal. Since this structure for the auxiliary signal recording also connects both the testing ear canal and the external environment by providing an air passage between them, it forms the pressure relief channel. The reason why this structure can effectively sense ear canal disturbance noise is further explained in the paragraphs follows. The microphone and speaker channels are tightly coupled to ensure that leakage at the channel-speaker or channel-microphone interfaces are minimal or non-existent. Furthermore, it may be appreciated that in the present embodiment the channels 816, 818 and 819 may easily be cleaned when the ear tip 824 is taken off from the probe 800.

Referring now to FIG. 8B, shown therein is a perspective view of the external features of the probe housing 804 and the probe body 806 along with the channels 816, 818 and 819 on its surface. Channel 817 is internal within the probe body 806 such that the tip of the channel 817 at the distal end of the probe body 806 (i.e. away from the probe cap 803) is sealed when the probe 800 is assembled. The side channels 816 and 819 are front facing and are physically coupled to internal channels (not shown) that lead to the speakers 850a and 850b. Therefore, the side channels 816 and 819 may be used to deliver the acoustic output of the speakers 850a and 850b during use. The upper channel 818 may be used to couple sound energy to the main microphone 832 while the lower channel 817 may be used to couple sound energy to the auxiliary microphone 834. In this regard, the upper channel 818 is physically coupled with an internal channel 810 that leads to the main microphone 832 while the lower channel 817 is physically coupled with an internal channel 808 that leads to the auxiliary microphone 834 (see FIG. 8C for internal channels 806 and 808). The main microphone 832 and the main microphone channels generally connect with a large opening at the probe tip to allow for efficient sound transmission to the main microphone 832 from the ear canal being tested. Alternatively, in some embodiments, the speakers and the channels coupled to the speakers may be vertically oriented while the microphones and the channels coupled to the microphones may be horizontally oriented. Generally, the speakers 832 and 834 and microphones 850a and 850b are tightly coupled to their respective internal channel so as to ensure that acoustic sealing at the interfaces between the sensors and their channel may be maintained.

Referring now to FIG. 8C, shown therein is a cross-sectional view of the DPOAE probe 800 along its longitudinal axis showing the internal structures of probe 800. The auxiliary microphone 834 connects to a pressure release structure comprising: (1) a small surface channel 815 formed by the probe body 806 and the ear tip 824 (see FIG. 8F) to provide an air passage from the subject's ear canal to a hole 814'; (2) the hole 814' that is connected to the small surface channel 815 and the internal channel 808 that leads to the auxiliary microphone 834; (3) the internal auxiliary microphone channel 808, in which the opening 817 at the probe tip is always sealed when assembled; and (4) an inner hole 823 in the latch pin 822 as shown in FIG. 8B which may connect the auxiliary microphone channel 808 to the external surroundings of the probe 800.

The small surface channel 815 may be used for pressure release and sensing, such that when the ear tip 824 is added onto the distal end of the probe body 806, the small surface channel 815 may form a narrow passage which only allows static pressure inside the ear canal to be released, and only allow low frequency sound/pressure wave which may arise from the disturbance noise within the ear canal being tested to pass through. Thus, most of the ambient noise energy may be blocked from passing to the ear canal. The hole 823 may allow the auxiliary microphone 834 to sense the ambient noise and the hole 814' together with surface channel 815 may allow the auxiliary microphone 834 to sense ear canal disturbance noise (such as noise caused by movement, blood pressure pulsation etc. and whose energy is mostly concentrated in the low frequencies range). In the present example embodiment, both disturbance noise (usually at low frequencies) in the ear canal and the ambient noise can be sensed simultaneously.

The probe tip 824 fits over the probe body 806 and is used for firmly fitting the DPOAE probe 800 into the subject's ear canal during use. The distal portion of the probe tip 824 is enlarged to enhance the fit within the subject's ear canal and to provide acoustic isolation and reduce ambient noise from entering the ear canal. An enlarged external view of the probe tip 824 is also shown in FIG. 8E. The probe tip 824 may be fabricated using any type of soft or flexible biocompatible material such as rubber or silicone and may be made into various sizes to accommodate different ear canal diameters.

FIG. 8F shows a cross-sectional view of the probe tip 824, probe body 806 and the probe cap 802 along with the PCB 830 when the probe 800 is fully assembled. As described earlier, the various internal holes and channels may be used for pressure release and for noise sensing. Specifically, in the present embodiment, hole 823, hole 814', small probe body surface channel 815 and internal channel 817 altogether may be considered to be the probe's pressure release channel. As shown in flow path 855, an air pathway between the enclosed ear canal and the external outside air environment may be established for pressure release via the surface channel 815 which engages the probe tip in the ear canal. Surface channel 815 connects with hole 814' which provides access to the auxiliary microphone channel 808. In turn, the auxiliary microphone channel 808 is connected with hole 823 to access the outside environment. Furthermore, the internal channel 817 is sealed at the tip using glue or plastic, since that channel is coupled to the auxiliary microphone 834.

Figure 9A:
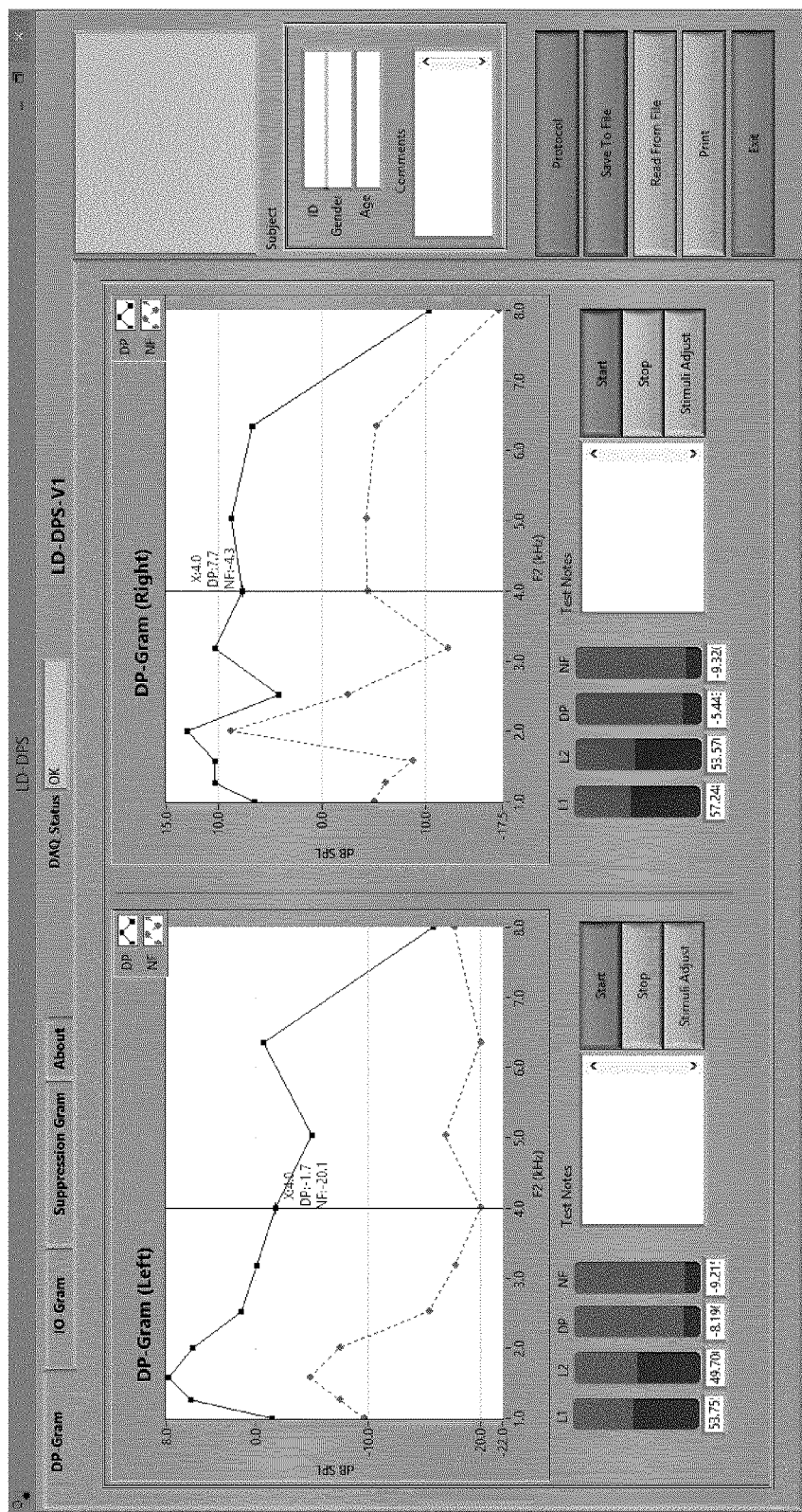
FIGS. 9A-9C are images of an example embodiment for a user interface for the DPOAE suppression detection system of FIG. 3.
Figure 9B:
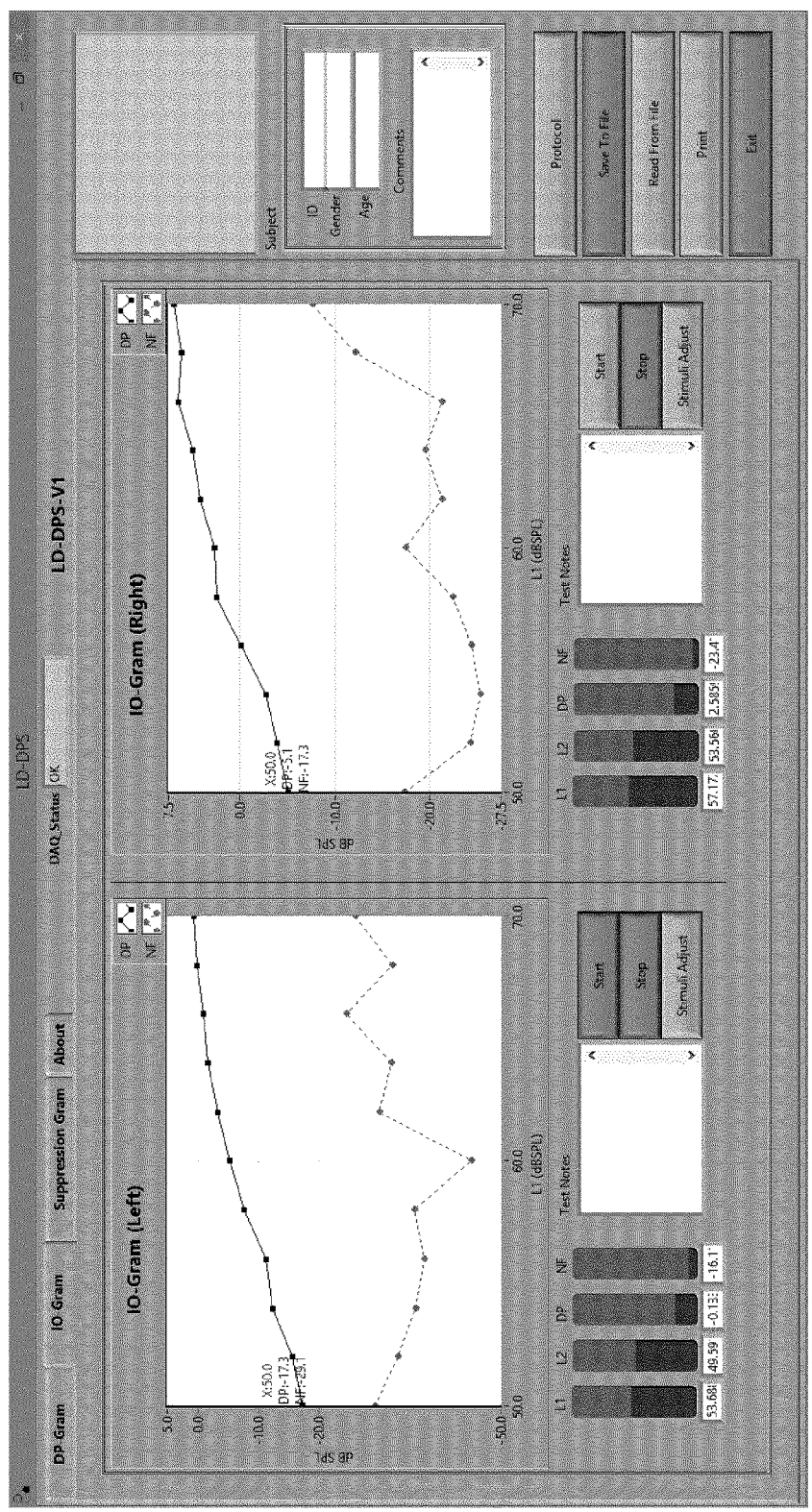
Figure 9C:
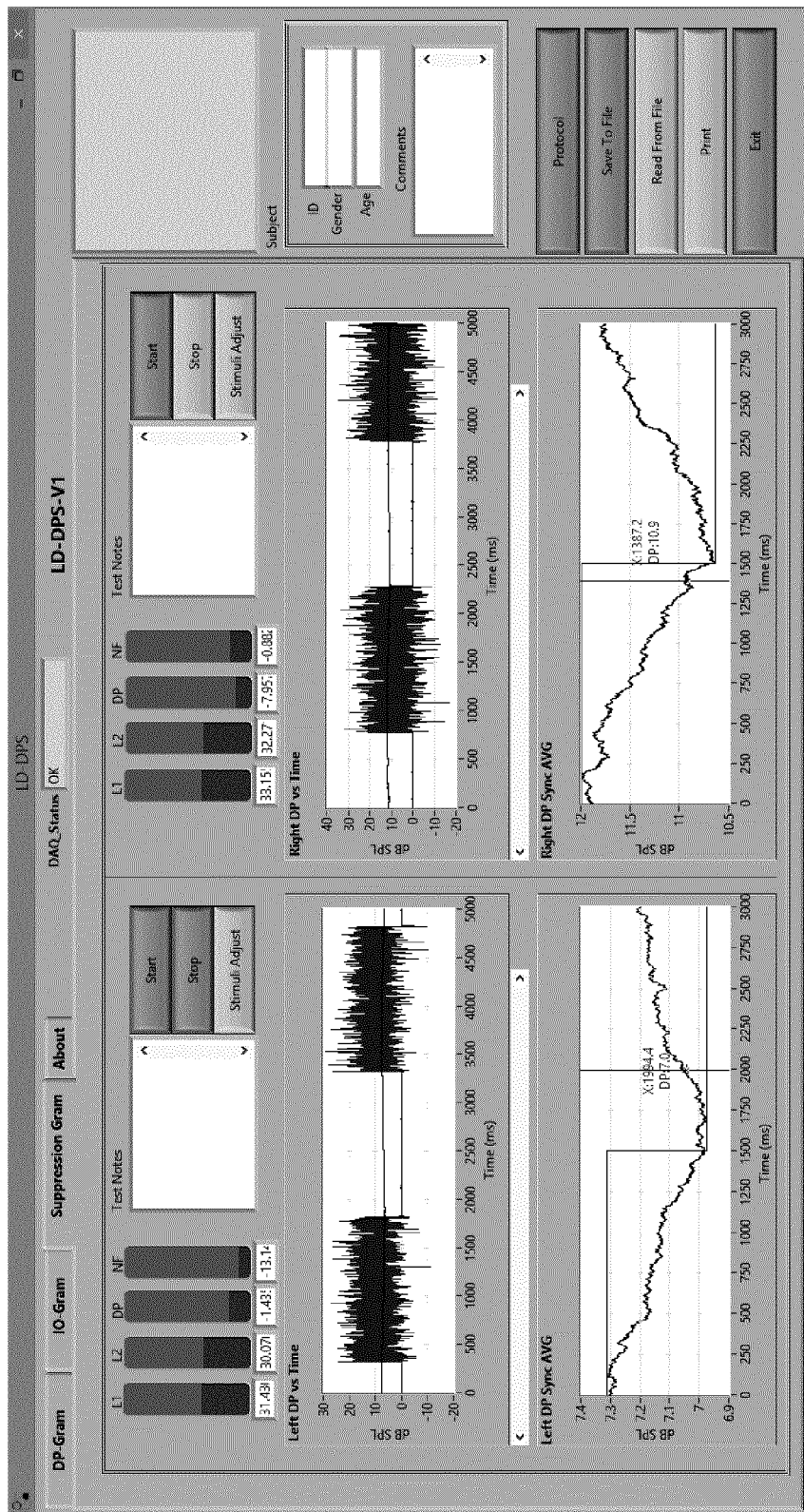

With respect to processing the signals obtained by the DPOAE probe 800, since the on-off time of the suppression inducing signal may be controlled and thus known, it may be possible to further improve detection during DPOAE suppression through using a synchronized averaging method. In this case, the estimated DP amplitude waveform may be divided into epochs within a data window of length equal to the period of the suppression inducing signal. During the DPOAE test, the epochs are recorded and averaged, and the running average may be presented to the clinician, for example, through an application user interface that may be used with the system 300, an example of which is shown in FIG. 9C. The configurable processing unit may provide additional user interfaces and control options as shown in FIGS. 9A and 9B to indicate to the clinician the measured DP signals and parameters. Specifically, FIG. 9A shows the DP-gram of the left and right ear which is a plot of the distortion product (DP) level as a function of f2 which is frequency of the second primary tone. FIG. 9B shows the DP IO-Gram of the left and right ear which is a plot of the DP level as a function of DPOAE stimulus parameter L1.

Example 2: Oscillometric Blood Pressure Monitoring of Blood Pressure Signals Contaminated With Continuous Motion Artifacts or From Subjects With Weak Pulses Clinically accepted automatic non-invasive blood pressure monitors (NIBP) fall into two categories. The first one being those based on the auscultatory method and the second one being those based on the oscillometric method.

In the auscultatory regime, an air pressure cuff may generally be placed around the subject's wrist or upper arm and an acoustic sensor may be placed under the cuff. The cuff is first inflated to a pressure above the systolic pressure which occludes arterial blood flow and then the cuff is deflated slowly. As the cuff pressure decreases, characteristic sounds (i.e. Korotkoff Sounds) may be detected when the cuff pressure corresponds to the subject's systolic and diastolic blood pressures.

In the oscillometric regime, estimates of blood pressure are based on pulse waveforms obtained when cuff pressure is applied during the inflation or removed deflation procedure. Generally, most commercially available automatic NIBPs use the oscillometric method. The SNR of the recorded cuff pressure waveform is important for measurement accuracy. Movement of the subject and ambient low frequency noise, weak cuff pressure pulses as seen in certain group of subjects such as those with obesity or critically ill, all lead to low SNR, and thus poor blood pressure measurement accuracy.

Many efforts have been made to improve the accuracy by detecting and rejecting movement artifacts (i.e. artifact rejection method). However, most of these attempts make use of a threshold method in which data collected during a subject's movement are simply discarded, which may lead to less useful data. In particular, such methods may not be suitable when the subject is in continuous movement, for example, during exercises and heart stress tests. An improvement to the artifact rejection method is to use a weighted average, i.e. assign a lower weight to noisy data and higher weights to quiet data leading to more usable data. However, if the noise and interference are dominant in the raw recordings, the weighted averaging method leads to very long processing time and/or a failure to detect the desired signal. Although the oscillometric method is less vulnerable than the auscultatory method to acoustic noise or artifacts, it still suffers from low frequency ambient noise and vibrations. For subjects with weak pulses, the artifacts and noise can significantly compromise measurement accuracy and may even make blood pressure measurements impossible. For these subjects, it is conventional practice to use a more complicated system in addition to a standard cuff based system. For example, for obese subjects, ultrasound Doppler may be used contemporaneously to detect the systolic and diastolic pressures.

Figure 10:
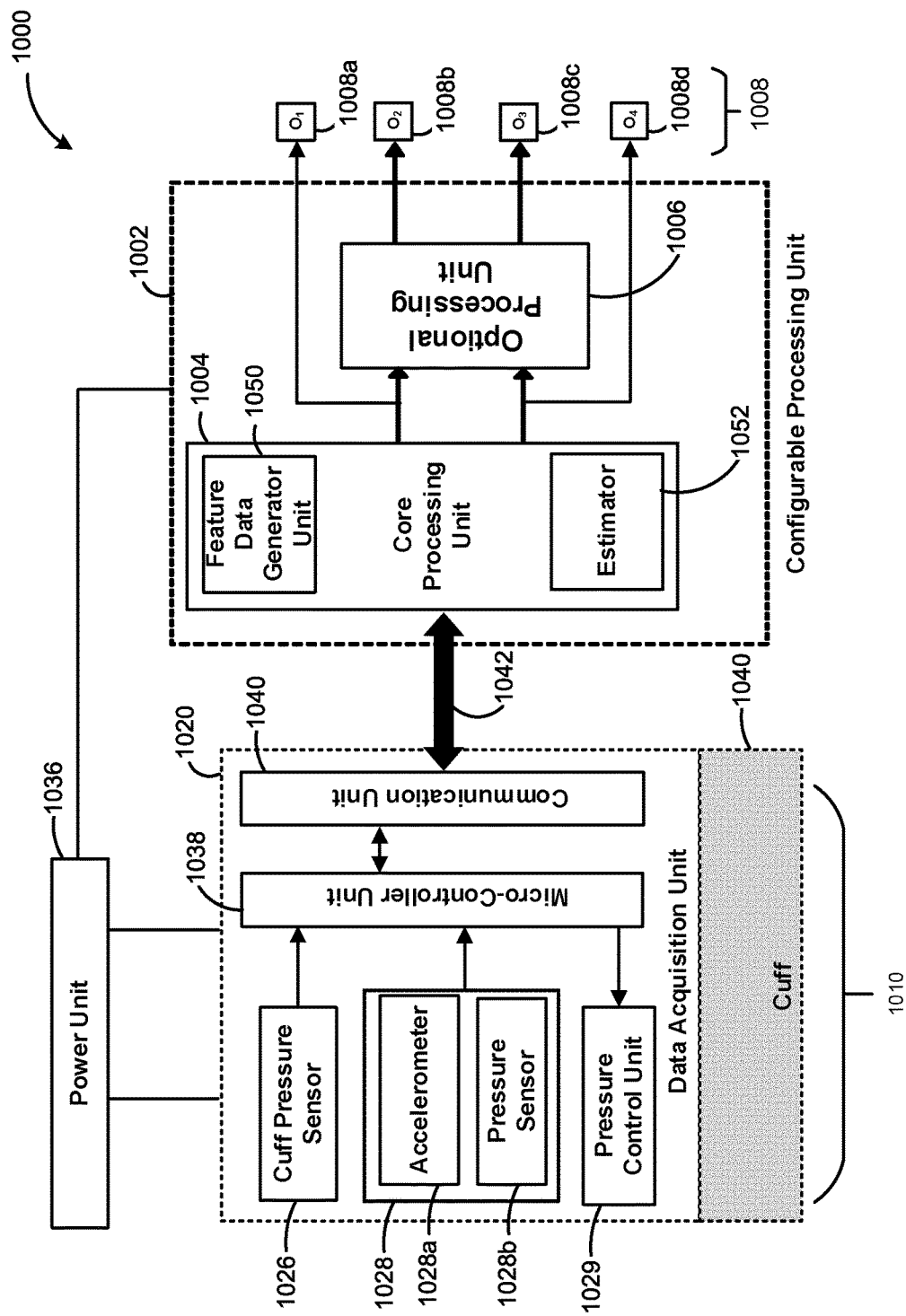
FIG. 10 is a block diagram of an example embodiment of a blood pressure monitoring system in accordance with the teachings herein.

Referring now to FIG. 10, shown therein is a block diagram of an example embodiment of a blood pressure monitoring system 1000 comprising a configurable processing unit 1002, a core processing unit 1004, an optional processing unit 1006, a sensor unit 1010, a feature data generator unit 1050 and corresponding signal processing methods to reduce ambient noise and motion artifacts and increase the SNR of the blood pressure measurements. The sensor unit 1010 includes a data acquisition unit 1020 and a blood pressure cuff 1025. The system 1000 also includes a power unit 1036 that may be an external power supply, or alternatively, an internal power source such as a battery. The power unit 1036 provides power to various components of the system 1000. The overall system configuration is similar to the signal detection system 100 of FIG. 1 as well as the DPOAE suppression detection system 300 of FIG. 3, as described previously.

In a standard oscillometric blood pressure test, an inflatable cuff is placed around the subject's upper arm or wrist. The cuff pressure waveform is collected during the inflation/deflation process. The collected cuff pressure waveforms are used to estimate the systolic and diastolic blood pressures. However, to improve blood pressure measurement, according to the teachings herein, additional sensor channels may be used with the data acquisition system to provide additional data that is processed to detect motion artifacts and ambient noise and remove them from the blood pressure measurements as described in more detail below.

Figure 11A:
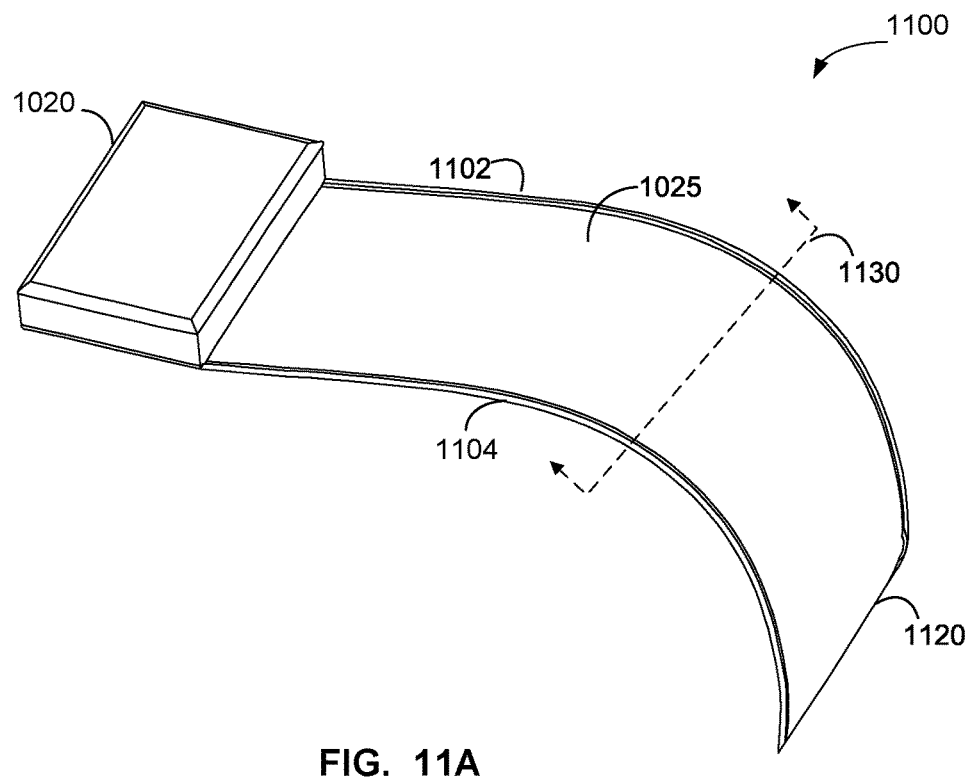
FIGS. 11A-11B show structural diagrams of example embodiments of a blood pressure measuring cuff and data acquisition unit of the blood pressure monitoring system of FIG. 10.

The sensor unit 1010 comprises the data acquisition unit 1020 and the cuff 1025 an example physical embodiment of which is shown in FIG. 11A. In the present example embodiment, the data acquisition unit 1020 may comprise a main cuff pressure sensor 1026 which performs a similar task as that of the main sensor 126 of FIG. 1, and an auxiliary sensor 1028 comprising an accelerometer 1028a and pressure sensor 1028b which together perform a similar task as that of the auxiliary sensor 128 of FIG. 1. Within the data acquisition of unit 1020, the various components may be mounted onto a printed circuit board (PCB). The accelerometer 1028a and pressure sensor 1028b may be configured to detect movement artifacts and ambient noise signals while the main cuff pressure sensor 1026 is recording data. Similar to the systems 100 and 300, the data acquisition unit 1020 comprises a microcontroller unit 1038 to control the acquisition of pressure signals, noise signals and artifact signals as well as to control the pressure control unit 1029 which adjusts the pressure applied by the cuff 1025 to the subject during pressure measurement. The acquired signals are sent to the configurable processing unit 1002 by the communication unit 1040 over the communications link 1042 using a similar implementation as described for the systems 100 and 300. In alternative embodiments, the combination sensor 1028 does not include an accelerometer. In these cases, the modeling and equations described below may be modified to account for not using an accelerometer.

To determine the blood pressure using the configurable processing unit 1002, the general methodology described previously with respect to adaptive signal processing may be applied herein. In other words, the quantities H(n) and X(n) may first be defined for this particular application and the processing described previously is used to obtain the desired signal, which in this case is the subject's blood pressure measurement. Z(n) is defined as the signal obtained from the main cuff pressure sensor 1026 (i.e. the main sensor) at sample instant n; Y(n) is the signal from the combination sensor 1028 (i.e. the auxiliary sensor) at sample instant n; and V(n) is the interference or noise coupled to the main cuff pressure sensor 1026. As described, Y(n)=[y(n) y(n−1) . . . y(n−q+1)] which is a 1×q matrix and V(n−1)=[v(n−1) v(n−2) . . . v(n−p)] which is a 1×p matrix. For blood pressure measurements, the recorded signal z(n) at sample instance n may be considered as the sum of a noise free cuff pressure at that sample instance and interference terms (e.g. v(n) of equation 4). If the noise free cuff pressure signal sample is defined as $x_s(n)$, then the feature vector may be written as $X_s(n)=[x_s(n)]$, Comparing this relationship with equation 7 above, the features matrix F(n) may be defined as being a single constant. For example, F(n)=[1]. These values together may be used to define the observation matrix H(n)=[F(n) ⋮ V(n−1) ⋮ Y(n)].

The interference strengths (i.e. the autoregressive coefficients) of the corresponding interference terms v(n−1) v(n−2) . . . v(n−p) may be defined as $a_1(n)$ $a_2(n)$ . . . $a_p(n)$. Additionally, the interference strengths (i.e. the moving average coefficients) of the corresponding interference terms y(n) y(n−1) . . . y(n−q+1) may be defined as $b_0(n)$ $b_1(n)$ . . . $b_{q-1}(n)$. These terms together may be used to form a linear system that establishes a link between the noise that is coupled to the main and auxiliary channels. As described previously in the signal model, the noise may be considered to originate from a common collective noise source from which the noise may be coupled to two linear systems corresponding to the main and auxiliary sensors. Also, as described previously, a relationship may further be established between main and auxiliary channels through the Autoregressive Moving Average, or ARMA model to model the noise and artifacts. Furthermore, $X_a$ may be defined as $X_a(n)=[a_1(n)\ a_2(n)\ \ldots\ a_p(n)]^T$ and $X_b$ may be defined as $X_b(n)=[b_0(n)b_1(n)\ \ldots\ b_{q-1}(n)]^T$ so that vector $X(n)$ may be $X(n)=[Xs(n)\ \vdots\ X_a(n-1)\ \vdots\ X_b(n)]^T$.

With these definitions established, the method 200 of FIG. 2 may be applied to remove the noise and motion artifacts from the cuff pressure sensor signal $Z(n)$. The estimated blood pressure measurement signal $\hat{X}_s(n)$ may then be used to provide the measured cuff pressure with an improved SNR. The systolic and diastolic pressures can then be estimated from the estimated blood pressure measurement signal $\hat{X}_s(n)$ using standard methods, such as the method based on oscillation envelope slope change during cuff deflation or the method based on the maxima of the envelope.

Figure 11B:
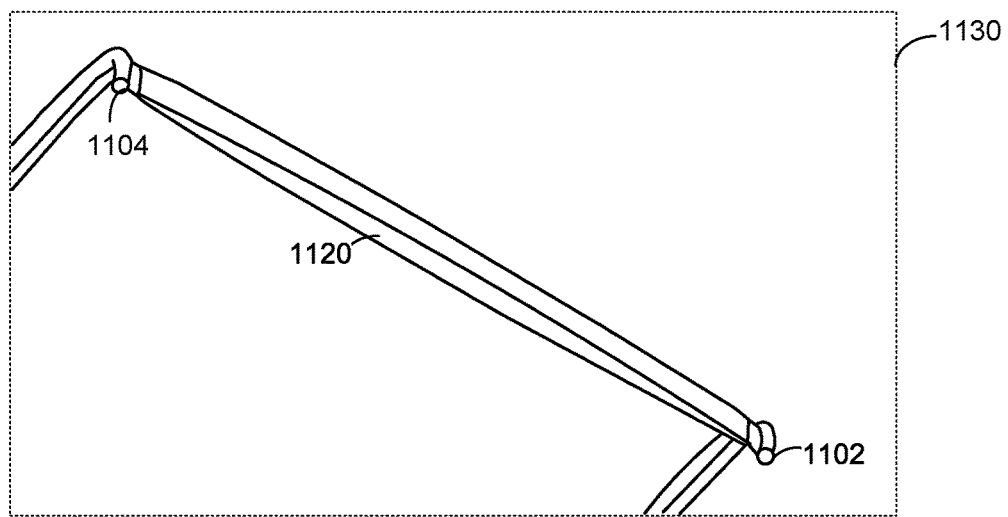

Referring now to FIGS. 11A and 11B, shown therein are structural views of an example embodiment of the sensor and data acquisition hardware, respectively, for the blood pressure monitoring system 1000. The data acquisition unit 1020 and the blood pressure cuff 1025 may be integrated into a single device. A first longitudinal edge of the blood pressure cuff 1025 comprises a first tube 1102 and a second longitudinal edge of the blood pressure cuff 1025 comprises a second tube 1104. The tubes 1102 and 1104 may be made from silicon or any other material capable of allowing other artifacts which may contaminate the desired signal to be sensed by the auxiliary pressure sensor. In some embodiments, both the first and second silicon tubes 1102 and 1104 may be connected to the auxiliary pressure sensor 1028b housed in the data acquisition unit 1020. Similarly, the accelerometer 1028a, which is configured to detect movement, may be fixed to a structure such as a printed circuit board in the data acquisition unit 1020. The auxiliary sensor 1028b, being configured to detect movement artifacts may help improve the SNR of the main cuff pressure sensor signal. The auxiliary sensor output data from these auxiliary sensors 1028a and 1028b form the $Y_i(n)$ in the observation matrix H(n).

The cross section line 1130 indicates the point of observation that is further depicted in FIG. 11B, corresponding to a position somewhere along the middle of the cuff 1025. Referring now to FIG. 11B, depicted therein is an enlarged sectional view of the main pressure bladder 1120 and the tubes 1102 and 1104. In the present example embodiment, a pump and valve system (not shown) may be connected to the bladder 1120 to allow the cuff 1025 to inflate and deflate. The distal end of the bladder 1120 as well as tube 1102 and tube 1104 (e.g. the portion of the bladder located away from the data acquisition unit 1020) is sealed to ensure that a constant pressure is maintained when the bladder 1120 is inflated. The main pressure bladder 1120 may be connected to the main cuff pressure sensor 1026 (i.e. the main pressure sensor) and used to collect cuff pressure data from which blood pressure waveforms are obtained during inflation and deflation of the blood pressure cuff 1025. The oscillometric blood pressure may thus be estimated based on the blood pressure waveforms after removal of the estimated noise and artifacts.

Example 3: Non-Invasive Continuous Blood Pressure Monitoring With Integrated Calibration Long-duration continuous blood pressure monitoring may provide significant value for the diagnosis of cardio-vascular problems, their intervention and critical care. However, standard cuff-based blood pressure monitors may not suitable for long-duration continuous blood pressure monitoring since at least one cuff inflation-deflation cycle (about one minute) is generally needed to obtain a single blood pressure measurement. Additionally, frequent cuff inflations and deflations can be intrusive to a subject's daytime activities and disruptive to the subject's night time sleep, making this method of blood pressure measurement not suitable for long term monitoring. Much work has been done with respect to the development of non-obstructive continuous blood pressure monitoring technologies. However, these conventional technologies are either uncomfortable for long time monitoring or need additional devices for calibration. However, in accordance with the teachings herein, systems and methods are provided that may integrate calibration and measurement steps into a single yet comfortable-to-wear device, which is suitable for long time continuous monitoring.

In accordance with the teachings herein, a blood pressure monitoring system similar to the system described in FIG. 10 may be adapted for long-duration and continuous monitoring. This may be done by deriving the arterial blood pressure from the measured cuff pressure waveform directly at a low constant cuff pressure. The cuff pressure may be controlled to be around or just below the diastolic pressure so that blood may flow freely along the artery under the cuff to minimize discomfort. Otherwise the interruption in blood flow would be felt by the subject during the monitoring.

In general, the cuff pressure waveform may be considered a function of: (1) the arterial blood pressure at the location of cuff deployment;

(2) the elastic compliance of the arterial blood vessel and surrounding tissue at the location of cuff deployment; and (3) the elastic compliance of the cuff. The relationship may be expressed as:

$$P_s - P_c = f(P_b - P_c) \tag{16a}$$

where $P_s$ is the pulse pressure measured by the main cuff pressure sensor 1026; $P_c$ is the mean cuff pressure derived from measurements of the main cuff pressure sensor 1026; and $P_b$ is the arterial pressure inside the blood vessel under the cuff 1025. The function $f(\ )$ may be non-linear as a result of non-linear compliance of the blood vessel.

To recover the arterial pressure $P_b$ the equation 16a above may be written as shown in equation 16b.

$$P_b - P_c = f^{-1}(P_s - P_c) = g(P_s - P_c) \tag{16b}$$

Assuming $g(\ )$ may be approximated by a Taylor series, equation 16b may be re-written as the following summation in equation 16c:

$$P_b - P_c = \Sigma_{i=0}^{K-1} d_i \times (P_s - P_c)^i + w \tag{16c}$$

where w represents the approximation error.

Comparing equation 16c with equation 7 above, it may be noted that $X_s$ corresponds to $[d_0\ d_1\ \ldots\ d_{K-1}]^T$ and that F corresponds to $[(P_s-P_c)^0\ (P_s-P_c)^1\ \ldots\ (P_s-P_c)^{K-1}]$ and V and Y are not applicable in equation 16c. Therefore, the method 100 described in FIG. 2 may be applied to estimate the coefficients $d_i$. In this case the values for $P_s$ and $P_c$ may be obtained from the main cuff pressure waveform $\hat{X}_s(n)$ as estimated in Example 2 described above and through a moving average of the estimated main cuff pressure waveform $\hat{X}_s(n)$. Specifically, $$P_c(n) = \frac{1}{N} \sum_{m=-\frac{M}{2}}^{M/2} \hat{X}_s(n+m) \qquad (16d)$$

$$P_s(n) = \hat{X}_s(n) \qquad (16e)$$

If the coefficients $d_i$ are known, then the arterial pressure $P_b$ inside the blood vessel under the cuff 1025 can be determined.

In general, the elastic compliance parameter of the cuff may depend on the mean cuff pressure $P_c$, arterial blood pressure at the location of cuff deployment, elastic compliance of the arterial blood vessel and the elastic compliance of the cuff so a more general formula for blood pressure measurement may use a multivariate function in the form $g(x,y)$, which may be expanded using multivariate Taylor expansion as shown in equation 16f.

$$P_b - P_c = g(P_s - P_c, P_c) \qquad (16f)$$

The multivariate Taylor expansion may use two variables in the Taylor Expansion Approximation as shown in the function $g(\ )$. Second and third order approximations are used in this example embodiment. It may be understood that higher order expansions may be obtained in a similar way.

For a function $u = g(x,y)$, the second order Taylor expansion at $(x_0, y_0)$ may be written as shown in equation 16g.

$$g(x_0 + \Delta x, y_0 + \Delta y) = \qquad (16g)$$
$$g(x_0, y_0) + g'_x(x_0, y_0)\Delta x + g_y(x_0, y_0)'\Delta y + \frac{1}{2}g''_{xx}(x_0, y_0)\Delta x^2 +$$
$$g''_{xy}(x_0, y_0)\Delta x \Delta y + \frac{1}{2}g''_{yy}(x_0, y_0)\Delta y^2 + O(\Delta x^3 + \Delta y^3)$$

When all of the coefficients are written as $d_i$ (i=0, 1, ... 5) and the error term as w, then equation 16g may be re-written as:

$$g(x_0+\Delta x, y_0+\Delta y) = d_0 + d_1\Delta x + d_2\Delta y + d_3\Delta x^2 + d_4\Delta x\Delta y + d_5\Delta y^2 + w \qquad (16h)$$

Letting $u=P_b-P_c$; $x=P_s-P_c$; $y=P_c$; $x_0=0$; $Y_0=P_{c0}$, then equation 16h can be assessed at $x_0=0$; $y_0=P_{c0}$, so that $\Delta x=P_s-P_c$, $\Delta y=P_c-P_{c0}$. In the present case $P_{c0}$ may be referred to as the reference pressure. Then, equation 16f above may be re-written as the second order equation 16i.

$$P_b - P_c = g(P_s - P_c, P_c) = d_0 + d_1(P_s - P_c) + d_2(P_c - P_{C0}) + \qquad (16i)$$
$$d_3(P_s - P_C)^2 + d_4(P_s - P_C)(P_c - P_{C0}) + d_5(P_C - P_{C0})^2 + w$$

Similarly, a third order equation may be derived as shown in equation 16j.

$$P_b - P_c = g(P_s - P_c, P_c) = d_0 + d_1(P_s - P_c) + \qquad (16j)$$
$$d_2(P_C - P_{C0}) + d_3(P_s - P_C)^2 + d_4(P_s - P_C)(P_c - P_{C0}) +$$
$$d_5(P_C - P_{C0})^2 + d_6(P_s - P_C)^3 + d_7(P_s - P_C)^2(P_c - P_{C0}) +$$
$$d_8(P_s - P_C)(P_c - P_{C0})^2 + d_9(P_C - P_{C0})^3 + w$$

Comparing the second order equation 16i with equation 7 above corresponding to the raw recording, it may be observed that:

$$X_s = [d_0 \, d_1 \ldots d_5]^T \qquad (16k)$$

$$F = [1 \, (P_s-P_C)(P_C-P_{C0})(P_s-P_C)(P_c-P_{C0})(P_C-P_{C0})^2] \qquad (16L)$$

and V and Y are not applicable in equation 16k, so that the observation matrix H may be fully defined by feature matrix F. Therefore, the method 100 described previously may be used to estimate the second order coefficients $d_i$.

For the third order expansion, comparing equation 16i and equation 7 above, it may be observed that:

$$X_s = [d_0 \, d_1 \ldots d_9]^T \qquad (16m)$$

$$F = [1 \, (P_s-P_C)(P_C-P_{C0})(P_s-P_C)^2(P_s-P_C)(P_c-P_{C0})P_c - P_{C0})^2(P_s-P_C)^3(P_s-P_C)^2(P_c-P_{C0})(P_s-P_C)(P_c-P_{C0})^2(P_s-P_C)^3] \qquad (16n)$$

and that V and Y are also not applicable to equation 16m, so that the observation matrix H may be fully defined by the feature matrix F. Therefore, the method 100 described previously may be used to estimate the third order coefficients $d_i$.

Based on the above relations, the coefficients $d_i$ may be obtained by performing a calibration method. An example embodiment of a calibration method 1200 that may be used is shown in the flowchart of FIG. 12.

Therefore, in accordance with the teachings herein, non-invasive continuous blood pressure monitoring with integrated calibration may be performed using calibration and continuous monitoring which may both use the same hardware shown in FIGS. 10, 11A and 11B.

Figure 12:
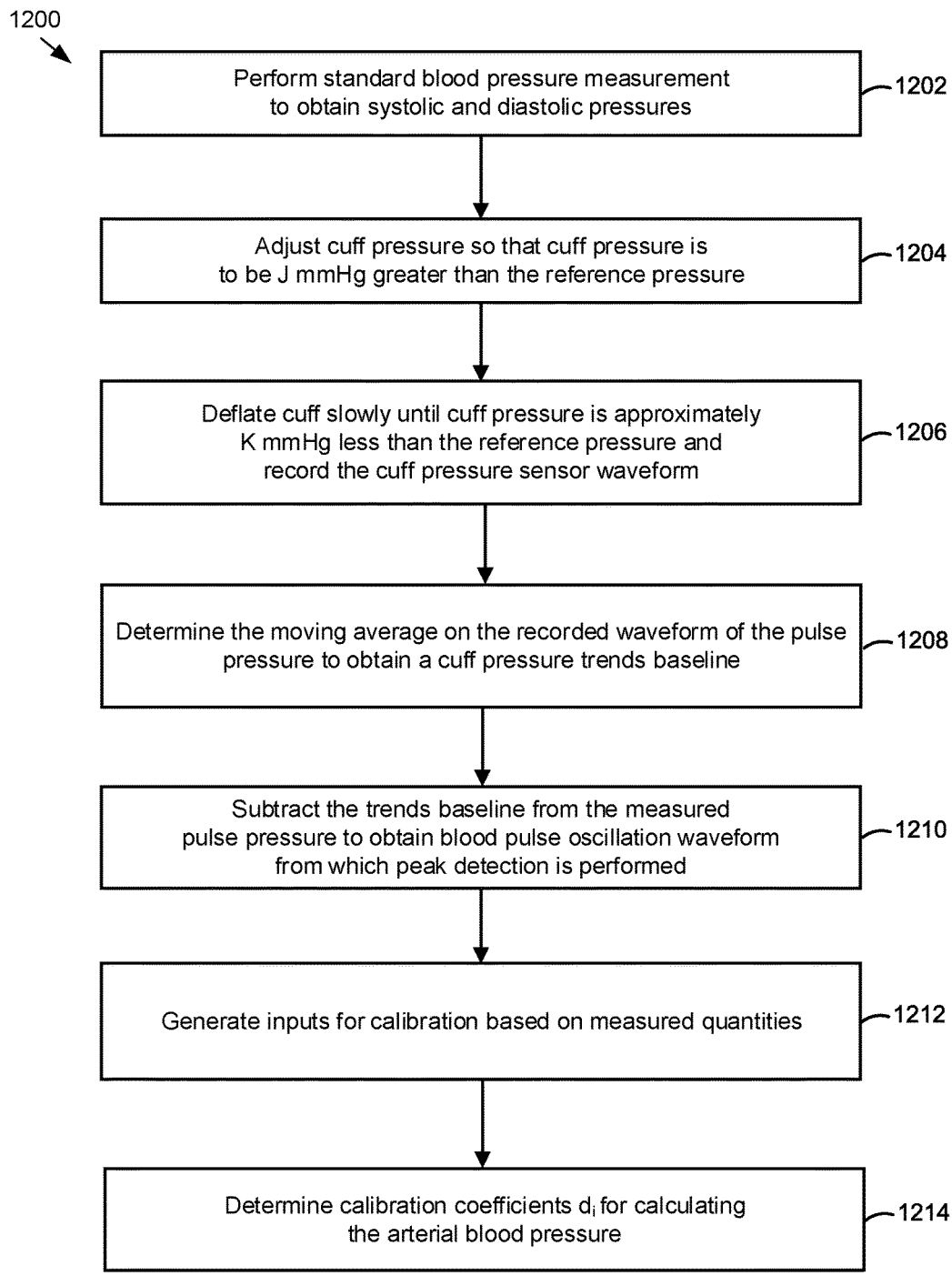
FIG. 12 is a flowchart of an example embodiment of a calibration method for continuous blood pressure monitoring in accordance with the teachings herein.

With respect to calibration, some calibration steps such as those in method 1200 of FIG. 12 may be used for continuous blood pressure monitoring. At act 1202, the systolic pressure $P_{sys}$ and the diastolic pressure $P_{dia}$ may be obtained using the blood pressure measurement system 1000 as previously described.

At act 1204, the mean cuff pressure $P_c$ is adjusted so that the mean cuff pressure is J mmHg greater than a reference pressure $P_{c0}$, which may be less than the diastolic pressure $P_{dia}$. In some embodiments, the quantity J may be approximately 10 mmHg and $P_{c0}$ can be set to be around 80 mmHg.

Figure 13A:
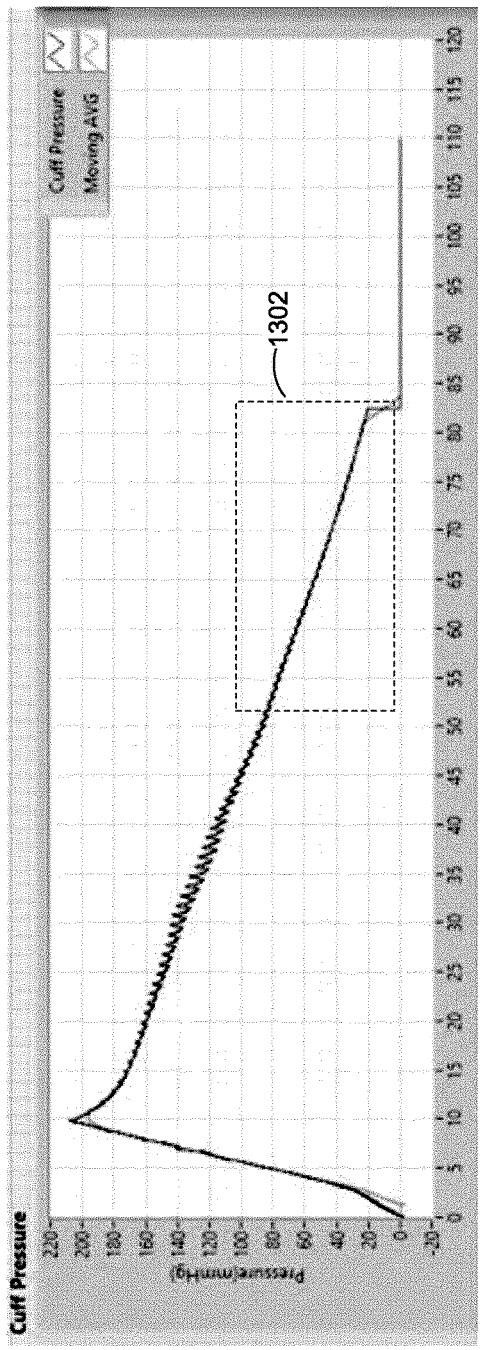
FIGS. 13A-13B show plots of measured cuff pressure at different rates of cuff deflation in accordance with the teachings herein.
Figure 13B:
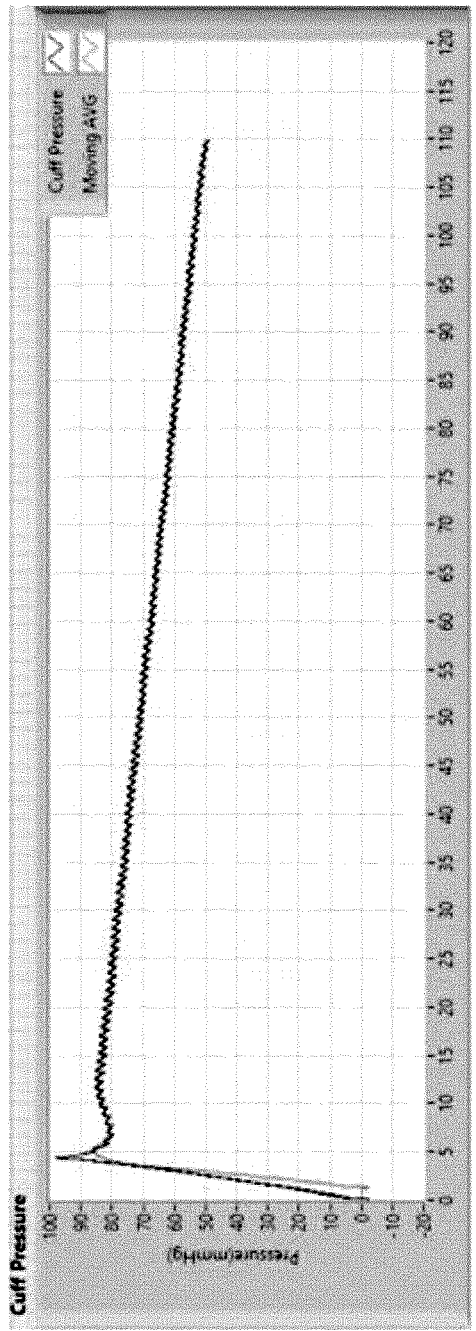

At act 1206, the blood pressure cuff may be deflated slowly until the mean cuff pressure $P_c$ is approximately K mmHg lower than the reference pressure $P_{c0}$, which is less than the diastolic pressure $P_{dia}$. Generally, under standard blood pressure testing, the deflation rate is typically 3-5 mmHg/sec, so that the time for the cuff pressure to decrease from 200 mmHg to 50 mmHg is about 30 to 50 seconds as shown in FIG. 13A. For subjects whose heart rate is approximately 60 beats per minute, approximately 30-50 pulses may be collected during the deflation period, making estimation of calibration more difficult and prone to inaccurate measurements since pulses may be less detectable due to low SNR as shown in the dashed box 1302. Thus, in some embodiments, the rate of deflation may be set to less than 0.5 mmHg/sec to enable collection of a sufficient number of pressure pulses with an acceptable SNR. For example, in some embodiments, a desirable amplitude of for pressure peaks may be about 10 times higher than the RMS noise. As shown in FIG. 13B, a slow rate of deflation allows more detectable pulses with an acceptable SNR to be collected when the cuff pressure is below the diastolic pressure. The cuff pressure sensor waveform $P_S$ may be recorded during deflation.

Figure 13C:
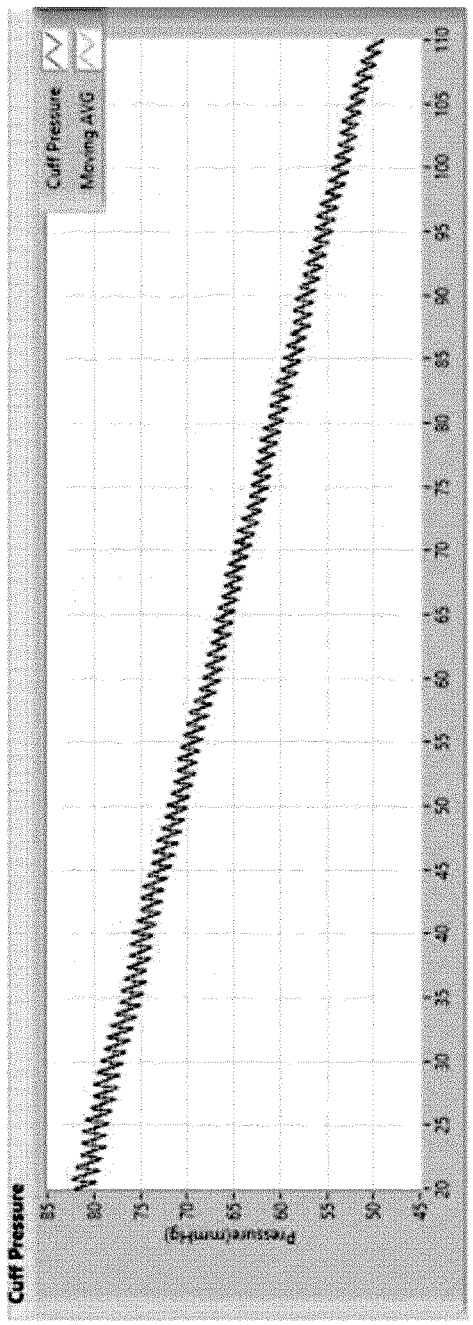
FIGS. 13C-13D show plots of the average cuff pressure and blood pulse oscillation waveform, respectively, in accordance with the teachings herein.

At act 1208, a moving average of the main cuff pressure sensor waveform $P_s$ (i.e. the mean cuff pressure $P_C$) may be recorded as shown in FIG. 13C. Note that this recorded moving average may also be called the cuff pressure trends baseline $P_c$. Hence, at least for the purpose of continuous blood pressure measurement, the mean cuff pressure and the cuff pressure trends baseline may be used interchangeably. For the purposes of the present teachings, and for consistency, the term "mean cuff pressure" is used.

Figure 13D:
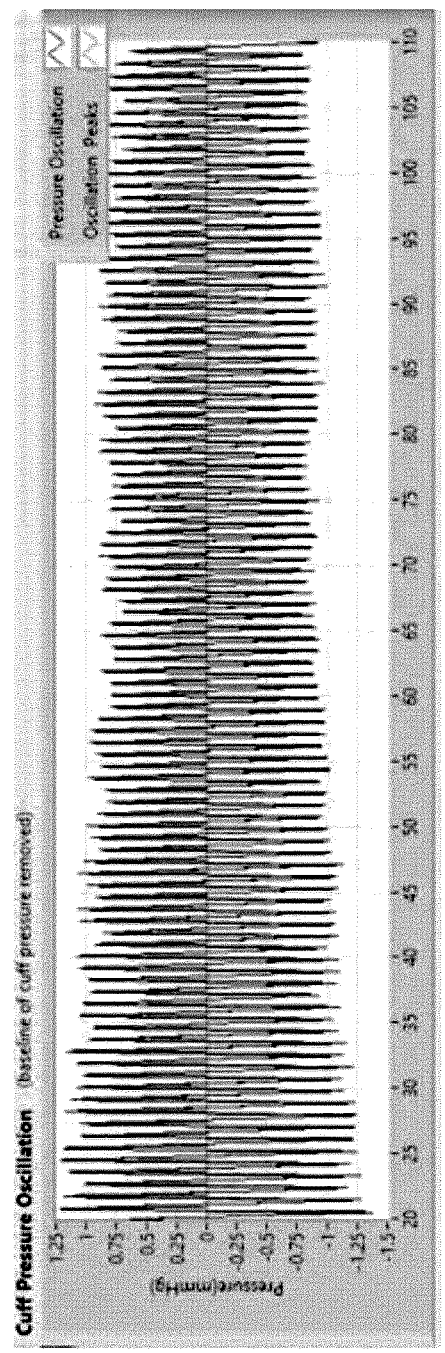
Figure 13E:
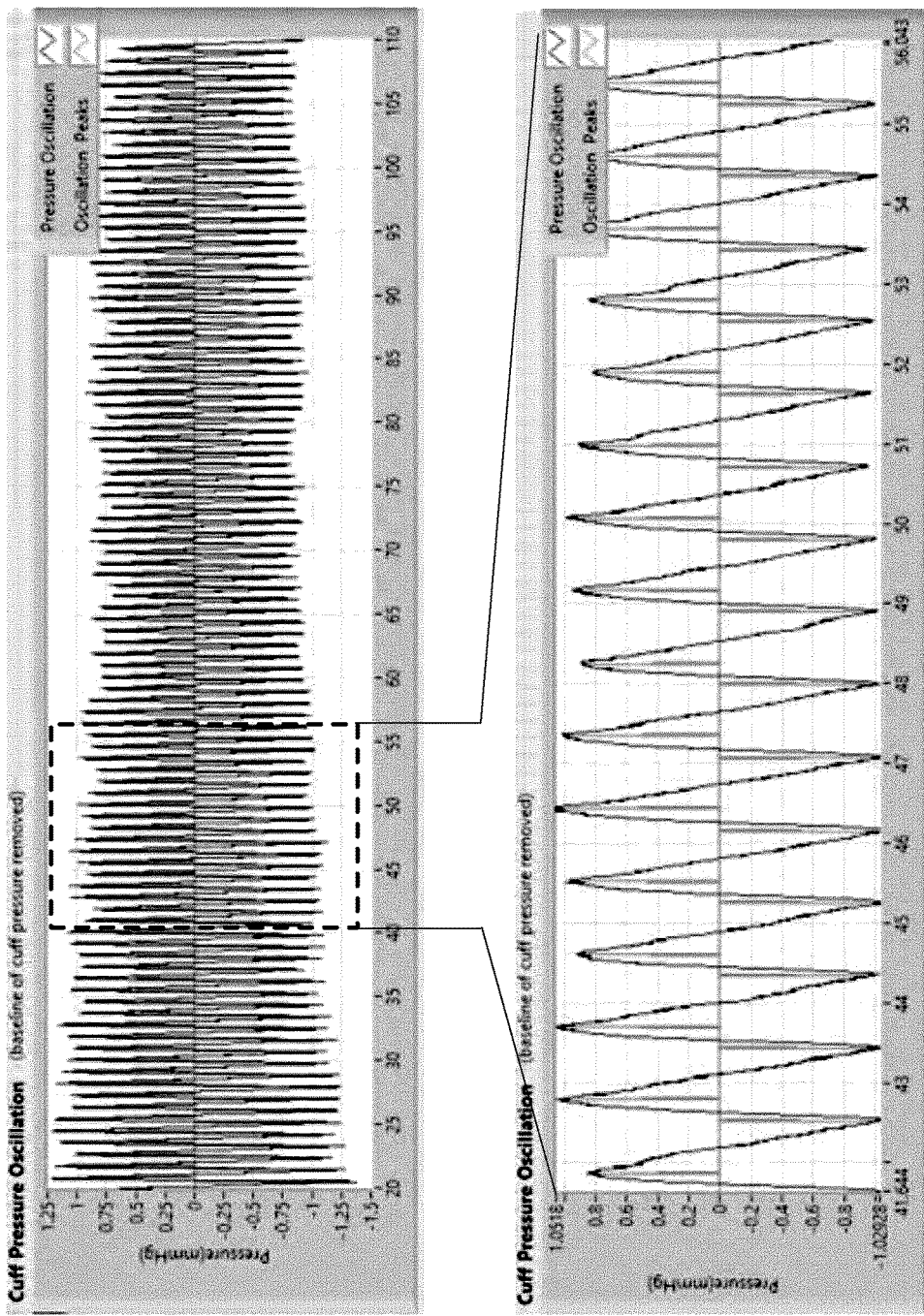
FIG. 13E shows an expanded view of the blood pulse oscillation waveform of FIG. 13D.

At act 1210, the mean cuff pressure $P_C$ may be subtracted from $P_S$ to obtain the blood pulse oscillation waveform $(P_s-P_C)$ as shown in FIG. 13D, from which peak detection can be performed to determine pulse peaks $P_{pk}(n)$. FIG. 13E is an expanded view of a portion of the waveform shown in FIG. 13D in which peaks and valleys may be identified.

Figure 13F:
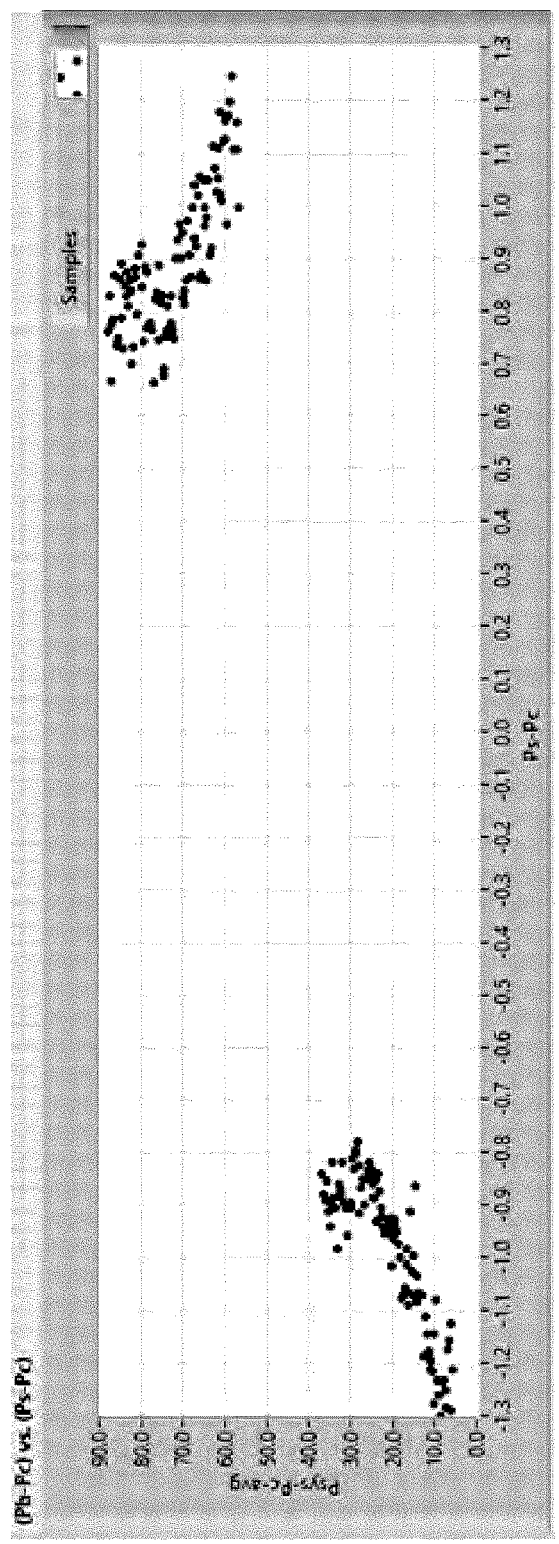
FIG. 13F shows a plot of the positive and negative pressure peaks corresponding to the time references of FIG. 13E in accordance with the teachings herein.

At act 1212, the inputs for the calibration (see e.g. equations 16i and 16j) may be generated. Specifically, the inputs include an array corresponding to the cuff pressure values $P_S$ at each peak; the reference cuff pressure $P_{c0}$; and an array constructed by setting the array elements to either the systolic pressure $P_{sys}$ or diastolic pressure $P_{dia}$, wherein the elements at positive peaks are associated to $P_{sys}$ and the elements corresponding to negative peaks may are set to $P_{dia}$ as illustrated in FIG. 13F. Specifically FIG. 13F shows a plot of the positive and negative peaks corresponding to the time reference of FIG. 13E. This plot may be obtained by examining all the peaks and valleys determined in a waveform such as the one shown in FIG. 13E. For example, for each pulse peak $P_{pk}(n_k)$, where k=0, 1, 2 . . . refers to the $k^{th}$ peak, $n_k$ may be used to indicate the time instant corresponding to the peak. Therefore, a point may be plotted on the plot shown in FIG. 13F at position $(P_{pk}(n_k)-P_c(n_k), P_{sys}-P_C(n_k))$ if the peak is a positive peak, and a point at position $(P_{pk}(n_k)-P_C(n_k), P_{dia}-P_C(n_k))$ may be established if the peak is a negative peak (i.e. a valley).

At act 1214, the calibration process represented by equations 16a-16n is performed to determine the calibration coefficients $d_i$ for determining the arterial blood pressure.

In this example embodiment, peak detection on the pulse pressure $P_s$ may be performed to form z(n), where n=0, 1, 2, . . . , k so that $P_s(n)$ corresponds to the $n^{th}$ peak that is detected. When using peak detection, z(n) may be re-written as:

$$z(n) = \begin{cases} P_{sys} - P_C(n) & \text{if } P_S(n) \text{ is a positive peak} \\ P_{dia} - P_C(n) & \text{if } P_S(n) \text{ is a negative peak} \end{cases} \quad (16n)$$

where $P_c(n)$ represents the baseline value of the mean cuff pressure at the $n^{th}$ peak.

H(n) and X(n) may be defined using equations 16k and 16L for the second order expansion and using equations 16m and 16n for the third order expansion. In general, the mean cuff pressure $P_C$ and the pulse pressure $P_S$ may use the corresponding values at the detected peaks, i.e. $P_c(n)$ and $P_S(n)$.

Y(n) and V(n-1) can be defined to be empty matrices. One can then define $F(n)=[1\ (P_s-P_C)\ (P_C-P_{C0})\ (P_s-P_C)(P_c-P_{C0})\ (P_C-P_{C0})^2]$ where $P_s$ and $P_C$ are cuff pressure and mean cuff pressure values at the peak positions and H (n)=[F(n)]. Furthermore, $X(n)=[d_0(n)\ d_1(n)\ \ldots\ d_5(n)]^T$.

To proceed with continuous blood pressure monitoring, the cuff pressure may be set to be the reference pressure $P_{C0}$ during operation. In practice however, it may be acceptable for the cuff pressure to deviate around the reference pressure by +/−1 mmHg as it is generally difficult to maintain an exact match to the reference pressure $P_{C0}$. Once the coefficients $d_i$ have been estimated, then the blood pressure waveform may be calculated.

From the second order expansion described in equation 16i, the blood pressure waveform may be determined as shown in equation 17a.

$$P_b = P_c + g(P_s - P_c, P_c) = P_c + d_0 + d_1(P_s - P_C) + d_2(P_c - P_{C0}) + \quad (17a)$$
$$d_3(P_s - P_C)^2 + d_4(P_s - P_C)(P_c - P_{C0}) + d_5(P_c - P_{C0})^2$$

Also, from the third order expansion described in equation 16j above, the blood pressure waveform may be determined as shown in equation 17b.

$$P_b = P_c + g(P_s - P_c, P_c) = P_c + d_0 + d_1(P_s - P_C) + \quad (17b)$$
$$d_2(P_C - P_{C0}) + d_3(P_s - P_C)^2 + d_4(P_s - P_C)(P_c - P_{C0}) +$$
$$d_5(P_C - P_{C0})^2 + d_6(P_s - P_C)^3 + d_7(P_s - P_C)^2(P_c - P_{C0}) +$$
$$d_8(P_s - P_C)(P_c - P_{C0})^2 + d_9(P_c - P_{C0})^3$$

The peaks of the arterial blood pressure $P_b$ may provide the systolic pressure while the valleys of the arterial blood pressure $P_b$ may provide the diastolic pressure. It may be possible to periodically re-calibrate coefficients $d_i$ based on periodically adjusting the cuff pressure around the diastolic pressure. This method may be possible because the diastolic pressure $P_{dia}$ corresponding to the critical cuff pressure point where the envelope has minimal slope (i.e. maximum negative slope) may be determined and use that point as a new $P_{dia}$ for calibration.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

REFERENCES

1. James A L, Mount R J, Harrison R V: Contralateral suppression of DPOAE measured in real time. Clin Otolaryngol 2002, 27:106-112.
2. Konomi U, Harrison R V, Kanotra S, James A. (2014) Age related changes to the dynamics of contralateral DPOAE suppression human subjects. J Otolaryngol Head Neck Surg. 2014 Jun. 16; 43:15. doi: 10.1186/1916-0216-43-15.
3. Wolter N E, Harrison R V, James A L. (2014). Separating the contributions of olivocochlear and middle ear muscle reflexes in modulation of distortion product otoacoustic emission levels. Audiol Neurootol. 2014; 19(1):41-8.
4. Stengel, Robert F. *Optimal control and estimation*. Courier Corporation, 2012.

The invention claimed is:
1. A method for adaptively detecting a desired signal S(n) in a noisy environment, the method comprising:
 obtaining a main signal Z(n) comprising the desired signal S(n) and at least one of noise and interference V(n) from a collective noise source;

obtaining an auxiliary signal Y(n) comprising at least one of a version of the noise and a version of the interference from the collective noise source; and at a processing unit:
generating a feature data set having at least one signal feature element for defining at least one feature of the desired signal;
generating noise and interference components corresponding to the at least one of noise and interference V(n) and the at least one of the version of the noise and the version of the interference Y(n);
estimating strengths of the at least one signal feature element and the noise and interference components corresponding to the at least one of noise and interference V(n) and the at least one of the version of the noise and the version of the interference Y(n); and
estimating the desired signal S(n) using the at least one signal feature element and the corresponding strengths and the noise and interference components corresponding to the at least one of noise and interference V(n) and the at least one of the version of the noise and the version of the interference Y(n) and the corresponding strengths.

2. The method of claim 1, wherein the method comprises using quasi-Kalman filtering for estimating the strengths and the desired signal by:
defining an observation matrix H(n) to include the at least one signal feature element and data values for the noise and interference components corresponding to the at least one of noise and interference V(n) and the at least one of the version of the noise and the version of the interference Y(n);
defining a state vector X(n) comprising the strengths for the at least one signal feature element and model parameters for the noise and interference components corresponding to the at least one of noise and interference V(n) and the at least one of the version of the noise and the version of the interference Y(n);
defining a state equation for X(n) based on a combination of X(n) for a previous time stamp X(n−1) and noise at a previous time stamp u(n−1); and
using a quasi-Kalman filtering method to estimate the state equation and the model parameters for the noise and interference components corresponding to the at least one of noise and interference V(n) and the at least one of the version of the noise and the version of the interference Y(n).

3. The method of claim 2, wherein the method comprises:
defining a time varying signal feature matrix F(n) by including at least one feature element of F(n) to provide a time series characterization of the at least one feature of the desired signal S(n);
defining a time varying noise and interference matrix, wherein a linear combination of elements in the time varying noise and interference matrix define the at least one of noise and interference V(n) of the main signal Z(n); and
representing the main signal Z(n) as a linear combination of elements of the state vector with coefficients for a linear combination being obtained from the observation matrix H(n) and then adding zero-mean white Gaussian noise, wherein the observation matrix H(n) comprises F(n), Y(n) and V(n).

4. The method of claim 3, wherein the method comprises constructing signal component waveforms by a linear combination of the state vector and said feature matrix.

5. The method of claim 3, wherein the method comprises constructing interference component waveforms by a linear combination of the state vector and the noise and interference matrix.

6. The method of claim 3, wherein the method comprises updating noise and interference matrix components using real time data from the auxiliary signal and using the state vector so the method performs adaptive filtering.

7. The method of claim 1, wherein the method comprises generating the at least one signal feature element from a closed-form formula, a look-up table or an actual recording having specific characteristics based on the desired signal that is to be detected.

8. The method of claim 1, wherein the method comprises relating the noise and interference components corresponding to the at least one of noise and interference V(n) and the at least one of the version of the noise and the version of the interference Y(n) by a linear system.

9. The method of claim 8, wherein the method comprises defining the linear system using a time-varying Autoregressive Moving Average (ARMA) model.

10. The method of claim 8, wherein the method comprises generating the noise and interference components corresponding to the at least one of noise and interference V(n) and the at least one of the version of the noise and the version of the interference Y(n) by using at least one of characteristics from noise and interference time functions, data from the auxiliary signal, and/or estimates provided by the processing unit thereby making the method adaptive to real data.

11. The method of claim 1, wherein the method comprises using a main sensor to obtain the main signal Z(n) and using an auxiliary sensor to obtain the auxiliary signal Y(n).

12. The method of claim 1, wherein the method is applied to Distortion Product Otoacoustic Emission (DPOAE) measurements, the method further comprising using a probe having two speakers to provide two stimulus tones to a subject, a main microphone to record the main signal Z(n) and an auxiliary microphone to record the auxiliary signal Y(n).

13. The method of claim 12, wherein the at least one signal feature element comprises signal features corresponding to a first stimulus tone, a second stimulus tone, and a DPOAE signal and the noise and interference components corresponding to the at least one of noise and interference V(n) and the at least one of the version of the noise and the version of the interference Y(n) are obtained from the auxiliary signal.

14. The method of claim 12, wherein the method is applied to DPOAE suppression measurements and the at least one signal feature element further comprises signal features corresponding to a tone with a frequency adjacent to a DPOAE tone for noise floor estimation.

15. The method of claim 13, wherein the method is applied to monitor an occurrence of middle ear muscle reflex (MEMR), by detecting a phase change of a primary tone or an intentionally introduced tone between a time period when a suppressor is on and when the suppressor is off, and determining the MEMR occurrence by comparing the phase change to a threshold.

16. The method of claim 3, wherein the method is applied to oscillometric blood pressure monitoring, the method further comprising using a blood pressure cuff with conduits for sensing a main pressure and an auxiliary pressure, a main pressure sensor to obtain the main signal Z(n), and a combination sensor having an auxiliary pressure sensor.

17. The method of claim 16, wherein the combination sensor further comprises an accelerometer to obtain the auxiliary signal Y(n), the accelerometer being used for sensing physical artifacts during monitoring.

18. The method of claim 16, wherein the at least one signal feature element is a single constant element and the noise and interference components corresponding to the at least one of noise and interference V(n) and the at least one of the version of the noise and the version of the interference Y(n) are based on data collected from the auxiliary signal.

19. The method of claim 16, wherein the estimated desired signal is used to estimate systolic and diastolic pressures using standard methods comprising determining oscillation envelope slope change during cuff deflation or determining a maxima of an envelope.

20. The method of claim 16, wherein the method is further applied to continuous blood pressure monitoring with integrated calibration, wherein:
the at least one signal feature element comprises elements [1  $(P_s-P_C)$  $(P_C-P_{C0})$  $(P_s-P_C)(P_c-P_{C0})$  $(P_C-P_{C0})^2$] wherein $P_c(n)$ corresponds to a moving average of a pressure imparted by the blood pressure cuff, $P_{C0}$ is a reference pressure, and $P_s(n)$ corresponds to a pressure peak or minimum of the blood pressure cuff at a moving average value $P_c(n)$;
the state vector is defined as $X(n)=X(n)=[d_0(n)\ d_1(n) \ldots d_5]^T$; and
the main signal $Z(n)=P_{sys}-P_c(n)$ or $Z(n)=P_{dia}-P_c(n)$ where $P_{sys}$ is an estimated systolic pressure and $P_{dia}$ is an estimated diastolic pressure.

21. The method of claim 20, wherein the noise and interference components corresponding to the at least one of noise and interference V(n) and the at least one of the version of the noise and the version of the interference Y(n) are set to zero and the observation matrix H(n) is defined by the signal feature matrix F(n).

22. The method of claim 21, wherein the method comprises determining a real time continuous blood pressure waveform according to:

$$P_b = P_c + g(P_s - P_c, P_c) = P_c + d_0 + d_1(P_s - P_C) + d_2(P_C - P_{C0}) + d_3(P_s - P_C)^2 + d_4(P_s - P_C)(P_c - P_{C0}) + d_5(P_C - P_{C0})^2.$$

23. The method of claim 20, wherein the strengths for the at least one signal feature element are obtained by performing calibration comprising:
determining a blood pressure measurement to obtain a systolic and a diastolic pressure;
setting a pressure applied by the blood pressure cuff to a value that is about J mmHg above the diastolic pressure;
decreasing the pressure applied by the blood pressure cuff at a rate that is less than 0.5 mmHg per second and recording a plurality of data pairs wherein each pair comprises a pulse pressure and a corresponding cuff pressure until the pressure applied by the pressure cuff is about K mmHg below the diastolic pressure;
identifying, from the plurality of data pairs, at least one data pair in which the pulse pressure corresponds to a detected pulse pressure peak or a detected pulse pressure valley; and
determining at least one calibration parameter based on the measured systolic pressure, diastolic pressure and the at least one identified data pair.

24. A computer readable medium, comprising a plurality of instructions executable on a processing unit for adapting the processing unit to implement a method of adaptively detecting a desired signal in a noisy environment wherein the method comprises:
obtaining a main signal Z(n) comprising the desired signal S(n) and at least one of noise and interference V(n) from a collective noise source;
obtaining an auxiliary signal Y(n) comprising at least one of a version of the noise and a version of the interference from the collective noise source; and
at a processing unit:
generating a feature data set having at least one signal feature element for defining at least one feature of the desired signal;
generating noise and interference components corresponding to the at least one of noise and interference V(n) and the at least one of the version of the noise and the version of the interference Y(n);
estimating strengths of the at least one signal feature element and the noise and interference components corresponding to the at least one of noise and interference V(n) and the at least one of the version of the noise and the version of the interference Y(n); and
estimating the desired signal S(n) using the at least one signal feature element and the corresponding strengths and the noise and interference components corresponding to the at least one of noise and interference V(n) and the at least one of the version of the noise and the version of the interference Y(n) and the corresponding strengths.

25. A system for adaptively detecting a desired signal S(n) in a noisy environment, the system comprising:
inputs for obtaining a main signal Z(n) and an auxiliary signal Y(n), the main signal comprising Z(n) comprising the desired signal S(n) and at least one of noise and interference V(n) from a collective noise source, and the auxiliary signal Y(n) comprising at least one of a version of the noise and a version of the interference from the collective noise source; and
a processing unit that is coupled to the inputs, the processing unit being configured to:
generate a feature data set having at least one signal feature element for defining at least one feature of the desired signal;
generating noise and interference components corresponding to the at least one of noise and interference V(n) and the at least one of the version of the noise and the version of the interference Y(n);
estimate strengths of the at least one signal feature element and the noise and interference components corresponding to the at least one of noise and interference V(n) and the at least one of the version of the noise and the version of the interference Y(n); and
estimate the desired signal S(n) using the at least one signal feature element and the corresponding strengths and the noise and interference components corresponding to the at least one of noise and interference V(n) and the at least one of the version of the noise and the version of the interference Y(n) and the corresponding strengths.

26. The system of claim 25, wherein the system further comprises a main sensor to obtain the main signal Z(n) and an auxiliary sensor to obtain the auxiliary signal Y(n).

27. The system of claim 25, wherein the processing unit is further configured to use quasi-Kalman filtering for estimating the strengths and the desired signal by:

defining an observation matrix H(n) to include the at least one signal feature element and data values for the noise and interference components corresponding to the at least one of noise and interference V(n) and the at least one of the version of the noise and the version of the interference Y(n);

defining a state vector X(n) comprising the strengths for the at least one signal feature element and model parameters for the noise and interference components corresponding to the at least one of noise and interference V(n) and the at least one of the version of the noise and the version of the interference Y(n);

defining a state equation for X(n) based on a combination of X(n) for a previous time stamp X(n−1) and noise at a previous time stamp u(n−1); and using a quasi-Kalman filtering method to estimate the state equation and the model parameters for the noise and interference components corresponding to the at least one of noise and interference V(n) and the at least one of the version of the noise and the version of the interference Y(n).

28. The system of claim 25, wherein the processing unit is further configured to perform Distortion Product Otoacoustic Emission (DPOAE) measurements and the system comprises a first probe having two speakers to provide two stimulus tones to a subject, a main microphone to record the main signal Z(n) and an auxiliary microphone to record the auxiliary signal Y(n).

29. The system of claim 28, wherein the processing unit is further configured to define the at least one signal feature element to comprise signal features corresponding to a first stimulus tone, a second stimulus tone, and a DPOAE signal and the noise and interference components corresponding to the at least one of noise and interference V(n) and the at least one of the version of the noise and the version of the interference Y(n) are obtained from the auxiliary signal.

30. The system of claim 29, wherein the processing unit is configured to perform DPOAE suppression measurements, the system comprises a second probe for generating a suppression tone, and the at least one signal feature further comprises signal features corresponding to a tone with a frequency adjacent to the DPOAE tone for noise floor estimation.

31. The system of claim 30, wherein the processing unit is configured to monitor for an occurrence of middle ear muscle reflex (MEMR), by detecting a phase change of a primary tone or intentionally introduced tone between a time period when a suppressor is on and when the suppressor is off, and determining the MEMR occurrence by comparing the phase change to a threshold.

32. The system of claim 28, wherein the first probe comprises a pressure release structure including:
a surface channel on a surface of a probe body and beneath an ear tip, the surface channel having a second end coupled to a first portion of an auxiliary channel that leads to the auxiliary microphone; and
a second channel having a first end that is coupled to a second portion of the auxiliary channel, the first end coupled closer to the auxiliary microphone, and a second end that is coupled to an external environment of the probe not covered by the ear tip.

33. The system of claim 32, wherein the surface channel has a first end forming a small passage to an ear canal being tested so that ambient noise and any other noise disturbances in the ear canal can be recorded as the auxiliary signal.

34. The system of claim 28, wherein the system further comprises:

a data acquisition unit for generating at least one stimulus to provide to at least one ear of a subject, and collecting response data for an ear under test; and a user interface to allow an operator to configure the system for performing audiometric tests and displaying the test results.

35. The system of claim 25, wherein the processing unit is configured to perform oscillometric blood pressure monitoring, the system further comprising a blood pressure cuff with conduits for sensing a main pressure and an auxiliary pressure, a main pressure sensor to obtain the main signal Z(n), and a combination sensor having an auxiliary pressure sensor.

36. The system of claim 35, wherein a first longitudinal edge of the blood pressure cuff comprises a first tube and a second longitudinal edge of the blood pressure cuff comprises a second tube, the tubes being made of material capable of allowing artifacts to be sensed by the auxiliary pressure sensor.

37. The system of claim 35, wherein the combination sensor further comprises an accelerometer to obtain the auxiliary signal Y(n), the accelerometer being used for sensing physical artifacts during monitoring.

38. The system of claim 35, wherein the system further comprises:
a pump and a valve system connected to a bladder of the blood pressure cuff to inflate and deflate the blood pressure cuff during use; and
a pressure control unit coupled to the pump and valve system to control the pressure applied to a user during use.

39. The system of claim 35, wherein the at least one signal feature element is a single constant element and the noise and interference components corresponding to the at least one of noise and interference V(n) and the at least one of the version of the noise and the version of the interference Y(n) are based on data collected from the auxiliary signal.

40. The system of claim 35, wherein the estimated desired signal is used to estimate systolic and diastolic pressures using standard methods comprising determining oscillation envelope slope change during cuff deflation or determining a maxima of an envelope.

41. The system of claim 35, wherein the processing unit is further configured to detect the desired signal S(n) in a noisy environment for continuous blood pressure monitoring with integrated calibration, wherein:
the at least one signal feature element comprises elements $[1 \ (P_s-P_C) \ (P_C-P_{C0}) \ (P_s-P_C)(P_c-P_{C0}) \ (P_C-P_{C0})^2]$ wherein $P_c(n)$ corresponds to a moving average of a pressure imparted by the blood pressure cuff, and $P_s(n)$ corresponds to a pressure peak or minimum of the blood pressure cuff at a moving average value $P_c(n)$;
a state vector is defined as $X(n)=X(n)=[d_0(n) \ d_1(n) \ \ldots \ d_5]^T$; and
the main signal $Z(n)=P_{sys}-P_c(n)$ or $Z(n)=P_{dia}-P_c(n)$ where $P_{sys}$ is an estimated systolic pressure and $P_{dia}$ is an estimated diastolic pressure.

42. The system of claim 35, wherein the system further comprises:
a data acquisition unit for collecting data from the main sensor and the combination sensor; and
a user interface to allow an operator to configure the system for performing at least one of blood pressure tests and blood pressure monitoring and for displaying results of the at least one of blood pressure tests and blood pressure monitoring.

* * * * *